US010602941B2

(12) United States Patent
Modur

(10) Patent No.: US 10,602,941 B2
(45) Date of Patent: Mar. 31, 2020

(54) PREDICTION OF PREICTAL STATE AND SEIZURE ONSET ZONES BASED ON HIGH FREQUENCY OSCILLATIONS

(71) Applicant: Ascension Texas, Austin, TX (US)

(72) Inventor: Pradeep N. Modur, Austin, TX (US)

(73) Assignee: ASCENSION TEXAS, Austin, TX (US)

( * ) Notice: Subject to any disclaimer, the term of this patent is extended or adjusted under 35 U.S.C. 154(b) by 36 days.

(21) Appl. No.: 15/639,429

(22) Filed: Jun. 30, 2017

(65) Prior Publication Data

US 2018/0000370 A1 Jan. 4, 2018

Related U.S. Application Data

(60) Provisional application No. 62/357,780, filed on Jul. 1, 2016.

(51) Int. Cl.
*A61B 5/04* (2006.01)
*A61N 1/36* (2006.01)
(Continued)

(52) U.S. Cl.
CPC ........ *A61B 5/04012* (2013.01); *A61B 5/0476* (2013.01); *A61B 5/4094* (2013.01); *A61N 1/36064* (2013.01); *A61N 1/36139* (2013.01); *A61B 5/0006* (2013.01); *A61B 5/0478* (2013.01); *A61B 5/4836* (2013.01);
(Continued)

(58) Field of Classification Search
CPC ............ A61B 5/04012; A61B 5/04014; A61B 5/0476; A61B 5/0494; A61B 5/0006; A61B 5/048; A61B 5/4836; A61B 5/7257; A61B 5/7282; A61N 1/36064
See application file for complete search history.

(56) References Cited

U.S. PATENT DOCUMENTS 8,600,513 B2 12/2013 Aur
2010/0292602 A1 11/2010 Worrell
(Continued)

OTHER PUBLICATIONS

Authorized Officer Lee W. Young, International Search Report and Written Opinion for International Application No. PCT/US2017/040315, dated Sep. 22, 2017, 13 pages.
(Continued)

*Primary Examiner* — Paula J Stice
(74) *Attorney, Agent, or Firm* — Norton Rose Fulbright US LLP

(57) ABSTRACT

A seizure preemption system including electrodes for recording simultaneous electroencephalographic (EEG) signals from a subject, a controller electrically coupled to the electrodes, and a neuromodulator electrically coupled to the controller. The controller is configured to sample the simultaneous EEG signals, identify high frequency oscillation (HFO) events in each EEG signal, and extract one or more features from each EEG signal to yield HFO profiles for the HFOs recorded from each EEG signal. Based on the HFO profiles for the EEG signal, the controller is configured to identify each EEG signal as associated with a preictal state or an interictal state of the subject. The neuromodulator is configured to deliver electrical stimulations to one or more seizure foci of the subject's brain via one or more of the electrodes in response to identification of at least one EEG signal as associated with a preictal state of the subject.

20 Claims, 15 Drawing Sheets

(51) Int. Cl.
*A61B 5/0476* (2006.01)
*A61B 5/00* (2006.01)
*A61B 5/0478* (2006.01)
*A61N 1/05* (2006.01)

(52) U.S. Cl.
CPC ........... *A61B 5/7203* (2013.01); *A61B 5/7257* (2013.01); *A61B 5/7264* (2013.01); *A61B 5/7275* (2013.01); *A61B 5/7282* (2013.01); *A61N 1/0529* (2013.01)

(56) References Cited

U.S. PATENT DOCUMENTS

| 2012/0150257 | A1 | 6/2012 | Aur |
| 2015/0335294 | A1 | 11/2015 | Witcher |
| 2016/0045127 | A1 | 2/2016 | Stacey |

OTHER PUBLICATIONS

Chengyuan Wu, 'Closed-loop Stimulation: An Investigational Treatment for Refractory Epilepsy', Dec. 2013, 5 pages.
Pradeep N. Modur et al., 'Seizure Localization Using Broadband EEG: Comparison of Conventional Frequency Activity, High Frequency Oscillations and Infraslow Activity', J Clin Neurophysiol. 29(4), Aug. 2012, 19 pages.
Andrade-Valenca LP, Dubeau F, Mari F, et al. Interictal scalp fast oscillations as a marker of the seizure onset zone. Neurology 2011;77:524-531.
Mark J. Cook et al., 'Prediction of seizure likelihood with a long-term, implanted seizure advisory system in patients with drug-resistant epilepsy: a first-in-man study.' Lancet Neurol 2013;12:563-571.
J. Engel Jr. et al., 'Practice parameter: Temporal lobe and localized neocortical resections for epilepsy: Report of the Quality Standards Subcommittee of the American Academy of Neurology, in association with the American Epilepsy Society and the American Association of Neurological Surgeons.' Neurology 2003; 60:538-547.
Emelie Hedegärd et al., 'Complications to invasive epilepsy surgery workup with subdural and depth electrodes: a prospective population-based observational study', J Neurol Neurosurg Psychiatry 2014; 85:716-720.
Patrick Kwan et al., 'Early Identification of Refractory Epilepsy', N Engl J Med, Feb. 2000; 342:314-319.
Pradeep N. Modur et al., 'Ictal High Frequency Oscillations in Neocortical Epilepsy: Implications for Seizure Localization and Surgical Resection', Epilepsia Oct. 2011, 52(10):1792-1801.
Pradeep N. Modur. 'High frequency oscillations and infraslow activity in epilepsy', Ann Indian Acad Neurol Mar. 2014; 17(Suppl 1):S99-S106.
Pradeep Modur et al., 'Interictal high-frequency oscillations (HFOs) as predictors of high frequency and conventional seizure onset zones', Epileptic Disord 2015; 17(4): 413-424.
Martha J. Morrell et al., 'Responsive Cortical Stimulation for the Treatment of Medically Intractable Partial Epilepsy', Neurology Sep. 27, 2011;77(13):1295-1304.
Maeike Zijlmans et al., 'High-frequency Oscillations as a New Biomarker in Epilepsy', Ann Neurol Feb. 2012;71(2):169-178.
Greg A. Worrell et al., 'High-frequency oscillations and seizure generation in neocortical epilepsy', Brain. 2004; 127:1496-1506.
Houman Khosravani et al., 'Spatial localization and time-dependant changes of electrographic high frequency oscillations in human temporal lobe epilepsy', Epilepsia. 2009; 50(4):605-616.
Allison Pearce et al., 'Temporal changes of neocortical high frequency oscillations in epilepsy', J Neurophysiol 2013; 110(5): 1167-79.

PREDICTION OF PREICTAL STATE AND SEIZURE ONSET ZONES BASED ON HIGH FREQUENCY OSCILLATIONS

CROSS-REFERENCE TO RELATED APPLICATION

This application claims priority to U.S. Patent Application Ser. No. 62/357,780, entitled "PREDICTION OF PREICTAL STATE AND SEIZURE ONSET ZONES BASED ON HIGH FREQUENCY OSCILLATIONS" and filed on Jul. 1, 2016, which is incorporated by reference herein in its entirety.

TECHNICAL FIELD

This invention relates to apparatus, systems, and methods for predicting a preictal state preceding seizure onset and treating imminent seizures.

BACKGROUND

Epilepsy affects 1% of the world's population. Epileptic seizures can be debilitating because of the associated involuntary motor phenomena and impairment of consciousness. Uncontrolled seizures can lead to poor quality of life, inability to maintain gainful employment, inability to drive, and premature death. About one-third of epilepsy subjects do not respond to medication treatment, and require surgical resection or neurostimulation to control their seizures. Surgical treatment tends to be successful in only one-half to two-thirds of subjects, depending on the specific brain region targeted. Intracranial recordings of a subject's seizures are often necessary to accurately localize the seizure focus prior to surgical resection or placement of implantable neurostimulator leads. Such intracranial recordings of a subject's seizures require a surgical procedure to place the electrodes on the brain surface or within the brain, followed by continuous video-electroencephalographic (EEG) monitoring for several days coupled with withdrawal of the antiseizure medications to induce seizures. This procedure typically involves several days of hospitalization and carries a significant risk of morbidity, including hemorrhage and infection.

For presurgical localization of the seizure focus in subjects with epilepsy, the seizure onset zone (SOZ) is commonly used as an indirect measure of the theoretical epileptogenic zone (EZ), although the correlation between the two may not always be accurate. Although evidence suggests that the SOZ defined by the electrode channels or contacts showing ictal high-frequency oscillations (HFOs) or infraslow activity may be superior to that defined by the conventional frequency activity (CFA), it does not obviate the need for obtaining ictal recordings.

SUMMARY

In a first general aspect, a seizure preemption system includes electrodes, a controller electrically coupled to the electrodes, and a neuromodulator electrically coupled to the controller. The electrodes record EEG signals from a subject. The controller is configured to sample the simultaneous EEG signals, identify HFO events in each EEG signal, extract one or more features from each EEG signal to yield HFO profiles for the HFOs recorded from each EEG signal, and, based on the HFO profiles for the EEG signal, identify each EEG signal as associated with a preictal state or an interictal state of the subject. The one or more features extracted from each EEG signal include a connectivity of each EEG signal. Connectivity is a measure of the number of the HFO events of the EEG signal that overlap with the HFO events of the other EEG signals. The preictal state is a defined length of time immediately preceding the onset of a seizure. The neuromodulator is configured to deliver electrical stimulations to one or more seizure foci of the subject's brain through one or more of the electrodes in response to identification of at least one EEG signal as associated with a preictal state of the subject.

Implementations of the first general aspect may include one or more of the following features.

In some cases, the interictal state is temporally separated from a seizure by a predefined length of time. In certain cases, the predefined length of time separating the interictal state from a seizure is one hour or two hours.

The electrodes of the seizure preemption system may be adapted for intracranial placement.

The controller may be configured to sample the simultaneous EEG signals at a rate sufficient to detect the HFO events. In certain cases, the controller is configured to sample the simultaneous EEG signals at a rate of at least 1000 Hz.

The connectivity of each EEG signal may be given by $$\frac{1}{N} \cdot \frac{1}{t} \sum_{i,j=1, j \neq i}^{N-1} HFO_{ij},$$

where $HFO_{ij}$ represents an overlap between HFO events occurring simultaneously in EEG signals i and j, N is the total number of EEG signals, and t is the total time of all EEG signals analyzed in minutes. In some cases, the overlap occurs when the absolute value of the difference between the starting time of the one of the HFO events in EEG signal i and the starting time of the one of the HFO events in EEG signal j is below a first value or when the absolute value of the difference between the ending time of the one of the HFO events in EEG signal i and the ending time of the one of the HFO events in EEG signal j is below a second value. In some cases, the first defined value and the second defined value used in determining overlap are equal. In certain cases, the first defined value is 10 ms.

The one or more features extracted by the controller from each EEG signal may include density. Density is the total duration of the HFO events of the EEG signal divided by the duration of the EEG signal. The one or more features extracted by the controller from EEG signal may also include peak frequency. Peak frequency is the mean of peak frequencies of the HFO events of the EEG signal. The one or more features extracted by the controller from EEG signal may also include log power. Log power is the mean of the logarithm of the average power of the HFO events of the EEG signal. The one or more features extracted by the controller from EEG signal may also include amplitude. Amplitude is the mean of the average amplitude of the HFO events of the EEG signal.

In some cases, the controller is configured to remove frequency components below a defined frequency threshold from each EEG signal. In certain cases, the defined frequency threshold is 70 Hz. Each HFO event may have a mean frequency above the defined threshold. In certain cases, the mean frequency threshold is at least 70 Hz. Each HFO event may have a total power exceeding a defined power threshold. Each HFO event may also have a duration exceeding a defined duration threshold. In certain cases, the duration threshold is 5 ms or 10 ms.

The preictal state and the interictal state of the subject may be distinct.

In some cases, based on the HFO profiles for the set of EEG signals, the controller is configured to identify each EEG signal as associated with a SOZ or a non-SOZ, in which the SOZ is inside the seizure focus and the non-SOZ is outside the seizure focus. Identification by the controller of each EEG signal as associated with a SOZ or a non-SOZ may include assessing the receiver operating characteristic (ROC) curves of the HFO profiles for the set of EEG signals based on a binomial logistic regression (BLR) model of reference HFO profiles with the SOZ as the dependent variable and identifying the SOZ of the subject as corresponding to the location of at least one of the electrodes for which the ROC cutoff exceeds a defined threshold. In certain cases, the defined threshold is 0.2. The reference HFO profiles may be derived from the subject.

Identifying each EEG signal as associated with a preictal state or an interictal state of the subject may include assessing the ROC of the HFO profiles for the set of EEG signals based on a BLR model of reference HFO profiles with state as the dependent variable and identifying the preictal state of the subject when the ROC cutoff exceeds a defined threshold. In certain cases, the defined threshold is 0.8. The reference HFO profiles may be derived from the subject.

In a second general aspect, a seizure prediction system includes electrodes for recording simultaneous EEG signals from a subject and a controller electrically coupled to the electrodes. The control is configured to sample the simultaneous EEG signals, identify the HFO events in each EEG signal, extract one or more features from each EEG signal to yield HFO profiles for the HFOs recorded from each EEG signal, and, based on the HFO profiles for the set of EEG signals, identify each EEG signal as associated with a preictal state or an interictal state of the subject. The one or more features extracted from each EEG signal include a connectivity of each EEG signal. Connectivity is a measure of the number of the HFO events of the EEG signal that overlap with the HFO events of the other EEG signals in the set of EEG signals. The preictal state is a defined length of time immediately preceding the onset of a seizure.

In a third general aspect, a seizure prediction system includes multiple electrodes and a controller electrically coupled to each of the multiple electrodes. Each of the multiple electrodes is configured to be positioned so as to record a respective EEG signal from a mammalian subject. The controller is configured to record data from each of the EEG signals over a length of time, the data recorded at a sufficient sampling rate for each signal, identify HFO events in the recorded data, determine, from the recorded data and the identified HFO events, a connectivity parameter for each signal, and identify whether the subject is in a preictal state, based at least in part on the determined connectivity parameters.

Implementations of the third general aspect may include one or more of the following features.

In some cases, the sampling rate for recording data is at least 1000 Hz.

The controller may be further configured to send an alert signal indicating that the subject is in a preictal state. The controller may also be configured to activate, in response to identifying that the subject is in a preictal state, one or more neuromodulators connected to the subject.

In a fourth general aspect, seizure preemption includes sampling multiple simultaneous EEG signals from a subject, identifying HFO events in each EEG signal, extracting one or more features from each EEG signal to yield an HFO profile for each EEG signal, identifying each EEG signal as associated with a preictal state or an interictal state of the subject based on the HFO profiles for the set of EEG signals, and delivering electrical stimulations to one or more seizure foci of the subject's brain in response to identification of the preictal state to preempt an imminent seizure. The one or more features extracted from each EEG signal include a connectivity of each EEG signal. Connectivity is a measure of the number of the HFO events of the EEG signal that overlap with the HFO events of the other EEG signals in the set of EEG signals. The preictal state is a defined length of time immediately preceding the onset of a seizure.

In a fifth general aspect, seizure prediction includes sampling multiple simultaneous EEG signals from a subject, identifying HFO events in each EEG signal, extracting one or more features from each EEG signal to yield an HFO profile for each HFO event, and, based on the HFO profiles for the set of EEG signals, identifying each EEG signal as associated with a preictal state or an interictal state of the subject. The one or more features extracted from each EEG signal include a connectivity of each EEG signal. Connectivity is a measure of the number of the HFO events of the EEG signal that overlap with the HFO events of the other EEG signals in the set of EEG signals. The preictal state is a defined length of time immediately preceding the onset of a seizure.

Implementations of the fifth general aspect may include one or more of the following features.

In some cases, an implementation of the fifth general aspect includes directing an implanted neuromodulator device to deliver electrical stimulations to a seizure focus within the subject's brain in response to identifying an EEG signal as associated with a preictal state.

An implementation of the fifth general aspect may include directing an implanted drug delivery system to deliver an antiseizure medication locally within the subject's brain, directing a drug delivery system to deliver an antiseizure medication to a region of the subject's body via a closed-loop drug delivery system.

In certain cases, an implementation of the fifth general aspect includes generating a warning to allow the subject or a caregiver to take appropriate precautions in the event a seizure occurs.

Advantages of the systems and methods described herein include obviating the need for obtaining ictal (seizure) recordings, preemption of imminent seizures, therefore potentially eliminating or reducing length of hospitalization and morbidity associated with epilepsy.

Thus, particular embodiments have been described. Variations, modifications, and enhancements of the described embodiments and other embodiments can be made based on what is described and illustrated. In addition, one or more features of one or more embodiments may be combined. The details of one or more implementations and various features and aspects are set forth in the accompanying drawings, the description, and the claims below.

DETAILED DESCRIPTION

High frequency oscillations (HFOs), which occur in a range of 70-500 Hz, are a type of electroencephalographic (EEG) waveforms that can be present at the time of seizure onset (ictal HFOs) or in between seizures (interictal HFOs). As used herein, "interictal state" generally refers to a state temporally separated from a seizure by a defined duration (e.g., at least one hour or at least two hours). Although the HFOs can be recorded with scalp or intracranial electrodes, the latter is more common, where the EEG data are obtained from the electrodes placed directly on the brain surface or within the brain substance. Interictal HFOs, characterized by a set of parameters, can be used to predict the location of seizure focus as well as to predict a preictal state. As used herein, "seizure focus" refers to the region of the brain that is presumed to generate the seizures, as determined by one or more tests including the seizure semiology captured by history or video recordings, electrical activity on the EEG, imaging findings, and so on; on the other hand, "SOZ" refers to the region of the brain that is presumed to generate the seizures, as determined specifically by the electrical activity on the EEG recordings. As used herein, "preictal state" generally refers to a defined length of time immediately preceding the onset of a seizure (e.g., five minutes immediately preceding a seizure). A preictal state is understood to be distinct from an interictal state, which implies that a seizure is not imminent. Prediction of the preictal state, and thus an imminent seizure, allows surgical planning for device-based seizure preemption therapies.

Figure 1:
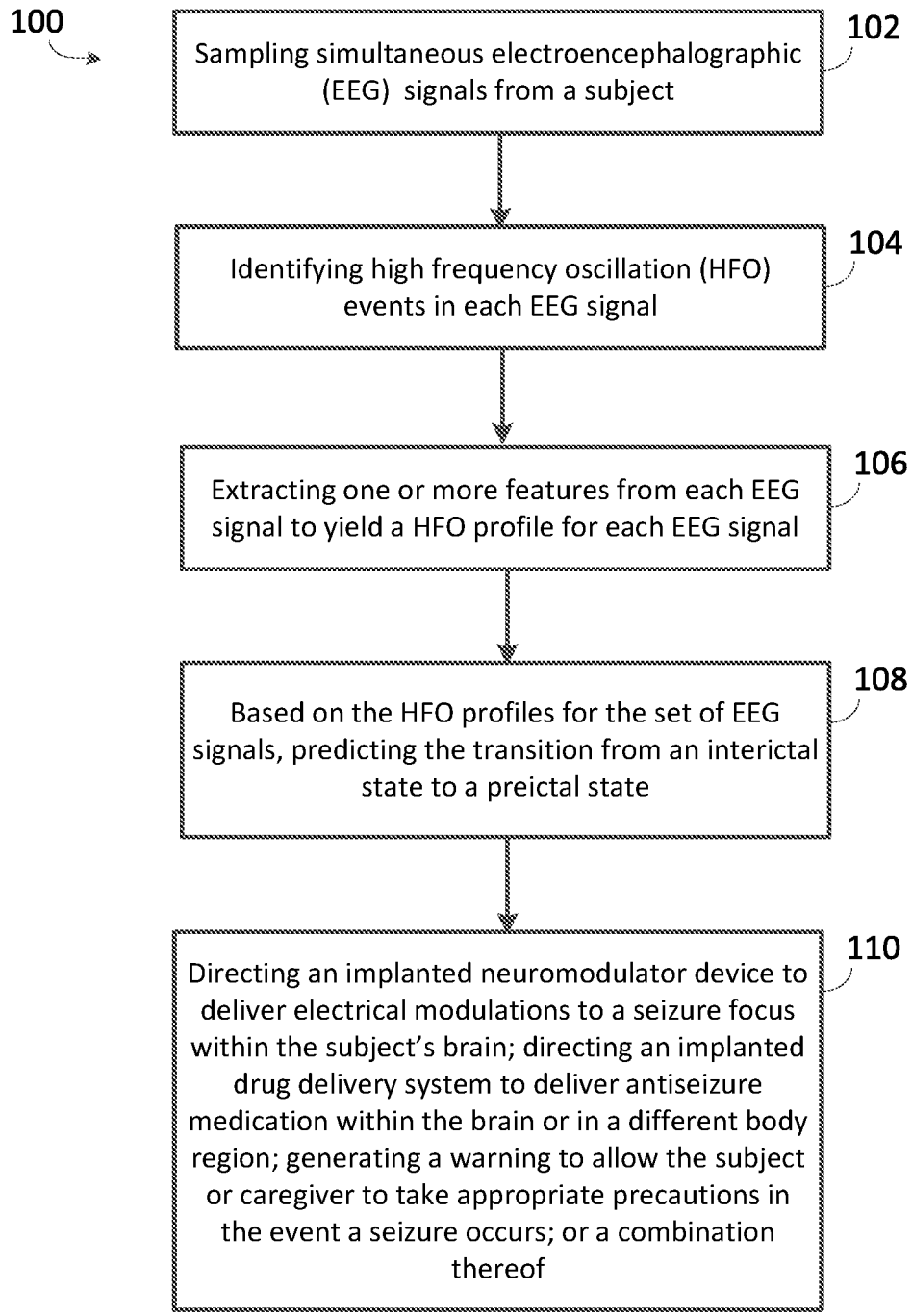
FIG. 1 a flowchart showing operations in process for preempting a seizure.

FIG. 1 is a flowchart showing the operations in process 100 for preempting a seizure. In 102, multiple simultaneous EEG signals (e.g., from different channels) from a subject are sampled. In 104, one or more HFO events, if present, are identified in each EEG signal. In 106, one or more features, including connectivity, density, peak frequency, log power, and amplitude, or combination thereof, are extracted from each EEG signal to yield a HFO profile for each EEG signal. In 108, based on the HFO profiles for the set of EEG signals, the transition from an interictal state to a preictal state is predicted, wherein the preictal state is a defined length of time immediately preceding the onset of a seizure. In 110, the system performs one or more of the following tasks or other similar tasks: (a) it directs an implanted neuromodulation device (neuromodulator) to deliver electrical stimulations to the seizure focus within the subject's brain in response to the identified preictal state to preempt an imminent seizure (closed-loop neuromodulation system); (b) it directs an implanted drug delivery system to deliver an antiseizure medication locally within the brain or remotely in a different body region (closed-loop drug delivery system); or (c) it generates a warning to allow the subject or caregiver to take appropriate precautions in the event a seizure indeed occurs (open-loop seizure warning system). As used herein, "neuromodulation" refers to the alteration of nervous system activity through the delivery of electrical stimulation or chemical agents to the targeted brain region, and "neuromodulator" refers to a device capable of accomplishing neuromodulation.

Figure 2:
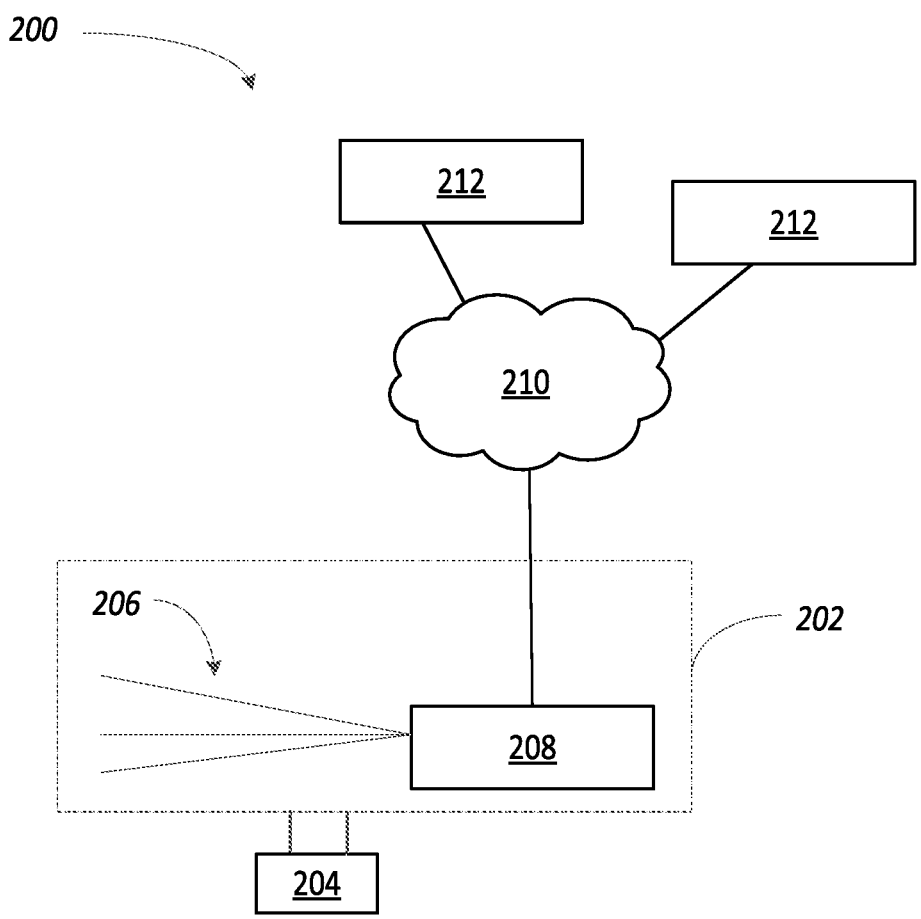
FIG. 2 depicts an exemplary seizure preemption system.

In some cases, process 100 includes one or more additional operations. In one example, process 100 may also include locating the SOZ of the subject. In certain cases, one or more operations may be omitted from process 100. In one example, 110 may be omitted, such that process 100 serves as a process for predicting a seizure. In still other cases, the order of one or more operations in process 100 may be interchanged. Implementations of process 100 may be understood with respect to features of seizure preemption system 200 depicted in FIG. 2.

Seizure preemption system 200 includes seizure prediction system 202 and neuromodulator 204. Neuromodulator 204 is linked to seizure prediction system 202. Seizure prediction system 202 includes electrodes 206 for accepting the multiple simultaneous EEG signals from a subject, and controller 208 for initiating the acquisition and processing of the EEG signals. Controller 208 is electrically coupled to electrodes 206 and neuromodulator 204. In some cases, controller 208 is linked to network 210, which allows remote computing device(s) 212 (for e.g., computers, beepers, hand-held devices, smartphones, smartwatches, etc.) to communicate with the controller.

Neuromodulator 204 is electrically coupled with the controller 208 and the electrodes 206. Upon identification of the preictal state, the controller 208 directs the neuromodulator 204 to deliver appropriate electrical stimulations to the subject's seizure focus using the electrodes 206 to preempt an impending seizure. In some cases, the controller 208 may direct the neuromodulator 204 to deliver an antiseizure medication or to generate a warning to the subject upon identification of the preictal state.

Electrodes 206 are configured to be electrically coupled to a subject's seizure focus, including the active HFO regions, intracranially or extracranially. The number and configuration of the electrodes may vary based on the size of the seizure focus and the active HFO region(s). In some examples, electrodes 206 are intracranial electrodes implanted in the subject's epileptogenic region, and include subdural strips, intracerebral depth electrodes, or both. In other examples, the electrodes 206 can be on the scalp surface or implanted under the scalp skin layer.

Controller 208 typically includes components such as analog-to-digital converter(s), digital-to-analog converter(s), filter(s), amplifier(s), signal processor(s), microprocessor(s), and the like. After initiating the acquisition of the simultaneous EEG signals via electrodes 206, the controller 208 processes the EEG signals and identifies the occurrence of a preictal state, which is distinct from the interictal state of the subject. Upon identification of the presence of the preictal state, the controller 208 may preempt the imminent seizure (ictal state) in the associated brain regions by initiating the delivery of electrical stimulation of that region via the neuromodulator 204.

The role of controller 208 in seizure prediction system 200 and seizure preemption system 202 may be understood in more detail as follows.

Simultaneous EEG signals provided to controller 208 via electrodes 206 may be sampled by the controller to yield a set of EEG features. Sampling occurs at a rate sufficient to ensure that HFOs of interest are captured. In one example, the simultaneous EEG signals are sampled at a rate of at least 1000 Hz.

Controller 208 is configured to automatically identify an HFO event, if present, in the EEG signal. As used herein, "HFO event" refers to a portion of the EEG signal that exceeds a minimum duration, contains a minimum number of statistically significant peaks, and either exceeds a mean frequency threshold or exceeds a threshold power in a defined frequency range. Automatically identifying the HFO events in the EEG signal includes processing of that signal. Processing of the EEG signal may include filtering the EEG signal, transforming the EEG signal, subjecting the EEG signal to a threshold function, removing sections of the EEG signal with signal discontinuities and artifacts, or any combination thereof. In one example, EEG signals are bandpass filtered at 50-333 Hz using a Butterworth 6-order zero-phase filter. In another example, the filtered EEG signals are subjected to Hilbert transform and a threshold function (e.g., 2 standard deviations above the mean Hilbert signal) is applied. The goal is to identify the candidate HFO events within the EEG signals. Candidate HFO events that meet or exceed a duration threshold and contain a minimum number of identifiable peaks are further processed to identify the definitive HFO events. In one example, an EEG signal segment that is ≥9 ms long and contains at least six peaks, two of which are at least four standard deviations above the mean rectified EEG signal, are further processed. Candidate HFO events in an EEG signal that occur sequentially and with a temporal spacing below a defined threshold may be combined into a single HFO event. In one example, the candidate HFO events that are less than 14 ms apart are combined to yield a single HFO event. A candidate HFO event is identified as a definitive HFO event if it exceeds a mean frequency threshold or exceeds a threshold power in a defined frequency range. In one example, a candidate HFO event is identified as an HFO event if it has a mean frequency of at least 70 Hz or has a total power in the range of 70-333 Hz that exceeds the total power below 70 Hz as calculated by fast Fourier transform (FFT).

For each of the identified HFO events, controller 208 extracts one or more features from the EEG signal to create an HFO profile. Features extracted from the EEG signal to create the HFO profile include at least one of connectivity, density, peak frequency, log power, and amplitude. In one example, controller 208 extracts all of these features from the EEG signal to characterize the identified HFO event. In another example, the controller extracts one, two, three, or four of connectivity, density, peak frequency, log power, and amplitude features from the EEG signal to characterize the identified HFO event.

Connectivity (number of connections per minute) is a measure of the network synchrony for a given EEG signal, defined as the sum of HFO events occurring simultaneously between the EEG signal and other EEG signals divided by the number of EEG signals sharing the simultaneous HFO events, normalized by the amount of data analyzed. Connectivity is given by:

$$\frac{1}{N} \cdot \frac{1}{t} \sum_{i,j=1, j \neq i}^{N-1} HFO_{ij}$$

where $HFO_{ij}$ represents an overlapping HFO event occurring simultaneously in EEG signals i and j, N is the total number of EEG signals, and t is the total time of all EEG signals analyzed in minutes. An HFO event may occur simultaneously when the absolute value of the difference between the starting time of the HFO event in EEG signal i and the starting time of the HFO event in EEG signal j is below a first value or when the absolute value of the difference between the ending time of the HFO event in EEG signal i and the ending time of the HFO event in EEG signal j is below a second value. The first and second values may be the same or different. In one example, the first and second values are the same and equal to 10 ms.

Density (ms/min) is a measure of the HFO events identified in each EEG signal given by the total duration of the HFO events in the EEG signal divided by the duration of the EEG signal analyzed. The use of density rather than rate as a feature removes the dependence of outcome based on the variations of the individual HFO event durations.

Peak frequency (Hz) is the mean of peak frequencies of the HFO events of the EEG signal. Higher peak frequency is generally understood to be a differentiating factor for HFO types.

Log power ($\mu V^2$) is the mean of the logarithm of the average power of the HFO events of the EEG signal. Higher log power is generally understood to be indicative of an HFO event associated with a seizure.

Amplitude ($\mu V$) is the mean of the average amplitude of the HFO events of the EEG signal.

HFO profiles for each EEG signal are fitted to at least one of a first binomial logistic regression (BLR) model configured to identify each EEG signal as originating from a SOZ or non-SOZ and a second BLR model configured to identify each EEG signal as associated with a preictal or interictal state. The first and second BLR models are based on the reference HFO profiles that were previously derived from the subject or from an independent group of reference subjects, respectively.

Identification of one or more EEG signals as being associated with the SOZ facilitates the determination of the spatial extent of the seizure onset in the subject. Identification of at least one EEG signal as being associated with a preictal state allows prediction of an imminent seizure by the seizure prediction system 202, preemption of the imminent seizure by the seizure preemption system 200, or both. In one example, upon identification of at least one EEG signal as associated with a preictal state, the controller 208 initiates the neuromodulator 204 to provide electrical stimulation to the electrode associated with EEG signal from which the identified EEG signal originated, thereby facilitating preemption of an imminent seizure. For the determination of the spatial localization of the SOZ, the controller 208 processes the data from each EEG signal provided by the electrodes 206 to construct the profiles for each identified HFO event. Each HFO profile consists of one or more features, including connectivity, density, peak frequency, log power, and amplitude. The controller 208 evaluates the HFO profiles dynamically in real-time using the coefficients derived from the BLR models constructed from a training cohort of subjects with a variety of epileptic seizure signatures. Based on such an analysis, the controller 208 determines the EEG signals that have a high probability of being in the SOZ. This information is then relayed to the devices connected to 212 to identify those signals constituting the SOZ. For the prediction of the preictal state, the controller 208 processes the EEG signals in the manner described above with some variations. The controller 208 evaluates the HFO profiles dynamically in real-time using the coefficients derived from the BLR models constructed from a training cohort of subjects with a variety of epileptic seizure signatures to determine the preictal state preceding the first seizure. Upon occurrence of the first seizure, the controller 208 reconstructs a new BLR model based on the HFO profiles constituting the subject's own individual preictal signature so that the new, subject-specific BLR model, tailored specifically to that subject, can be used for a more accurate identification of the subsequent preictal states in that subject. Upon identification of one or more of the EEG signals as being in the preictal state, the controller 208 directs the neuromodulator 204 to deliver electrical stimulations to one or more of the contacts of the electrodes 206 to preempt an imminent seizure. In a second example, the controller 208 directs the drug delivery system 204 to administer an antiseizure medication either locally within the brain or remotely in a different part of the body to preempt an imminent seizure.

EXPERIMENTAL

Interictal HFOs and SOZs

The relationship between the interictal HFOs and the SOZs defined by the ictal HFOs or conventional frequency activity (CFA) was assessed to evaluate the usefulness of the interictal HFOs as spatial markers of the SOZs. Seizures showing discrete HFOs at onset on intracranial EEGs acquired at ≥1000-Hz sampling rate in a training cohort of 10 subjects with temporal and extratemporal epilepsies were analyzed. Each ictal channel was classified as: HFO+ (HFOs at onset with subsequent evolution), HFO− (HFOs at onset without evolution), CFA (1.6-70-Hz activity at onset with evolution), or non-ictal. The SOZs were defined as: hSOZ (HFO+ channels only), hfo+&−SOZ (HFO+ and HFO− channels), and cSOZ (CFA channels). Using automated methods, the interictal HFOs were detected, and the following five features were extracted: density, connectivity, peak frequency, log power, and amplitude. Binomial logistic regression (BLR) models were created using these features, and their performance was tested in a separate replication cohort of three subjects. The models containing the five interictal HFO features reliably differentiated the channels located inside the SOZ from those outside in the training cohort (p<0.001), reaching the highest accuracy for the classification of hSOZ. Log power and connectivity had the highest odds ratios, both being higher for the channels inside the SOZ compared with those outside the SOZ. In the replication cohort of novel subjects, the same models differentiated the HFO+ from HFO− channels, and predicted the extents of the hSOZ and hfo+&−SOZ (F1 measure>0.5) but not the cSOZ. Interictal HFOs were shown to be useful in defining the spatial extent of the SOZ, and predicting whether or not a given channel in a novel subject would be involved in the seizure. The findings support the existence of an abnormal network of tightly-linked ictal and interictal HFOs in subjects with intractable epilepsy.

Subject Population.

Two cohorts of subjects were recruited for the study: a training cohort for developing the logistic regression models and a replication cohort for testing the models. All subjects were evaluated according to a standard presurgical protocol to determine the need, type of electrodes, and extent of coverage for intracranial monitoring. The inclusion criteria were: intracranial recordings acquired with a 1000-Hz sampling rate or higher; well-defined electrical seizure onset preceding the clinical seizure onset; and at least one seizure showing discrete HFOs at onset (>70-Hz activity, >400-ms duration). Subjects for whom adequate interictal data were not archived were excluded. Informed consent was obtained from all subjects.

Intracranial Recordings.

The EEGs for the training and replication cohorts were acquired on the 128-channel Nihon-Kohden (Nihon-Kohden, Foothill Ranch, Calif.) and Stellate (Natus Inc., San Carlos, Calif.) systems, respectively. The sampling rate of 1000 Hz allowed reliable visualization of activity up to 333 Hz. The implanted electrodes consisted of subdural grids and strips, intracerebral depth electrodes, or both, obtained from the same manufacturer (Ad-Tech Medical, Racine, Wis.).

Definition of SOZs.

Briefly, the clinical seizure onset was first marked by the earliest observable behavioral change on the video. Second, the occurrence of clear rhythmic activity in the CFA range was marked using bipolar montages, 1.6-70-Hz bandpass with 60-Hz notch filter, and 10-s/page window; conventional electrographic onset was then defined by tracing backwards to identify the timing of the earliest occurrence of discrete ≤70-Hz rhythmic activity. Third, the ictal HFO-based SOZ was defined by identifying all the channels that showed discrete HFOs within a 2-s window around the time of conventional seizure onset using bipolar montages, 53-300-Hz bandpass with 60-Hz notch filter, and 2-s/page window.

Figure 3A:
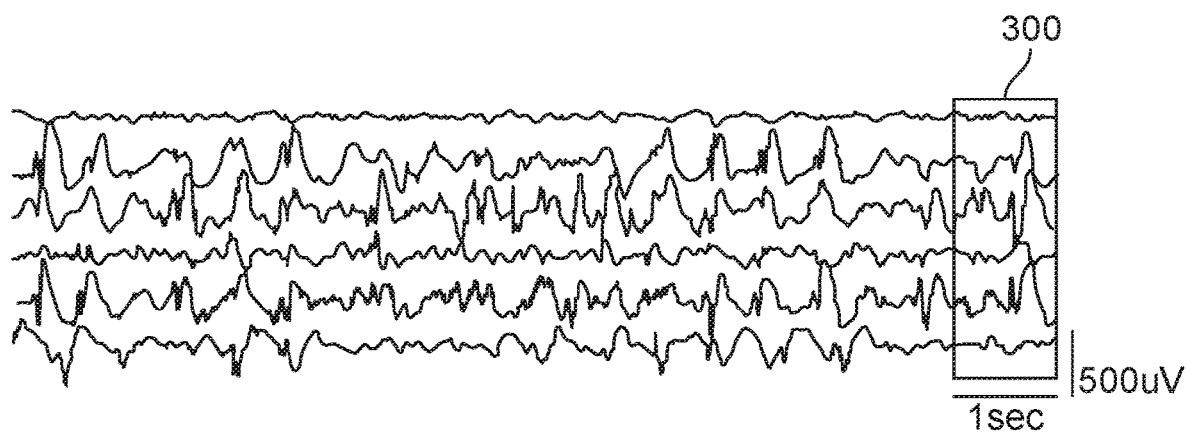
FIGS. 3A-3C depict visual identification of the interictal high-frequency oscillations (HFOs).
Figure 3B:
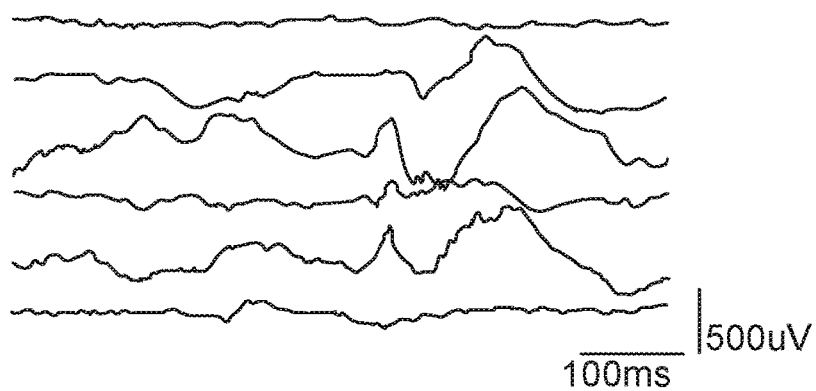
Figure 3C:
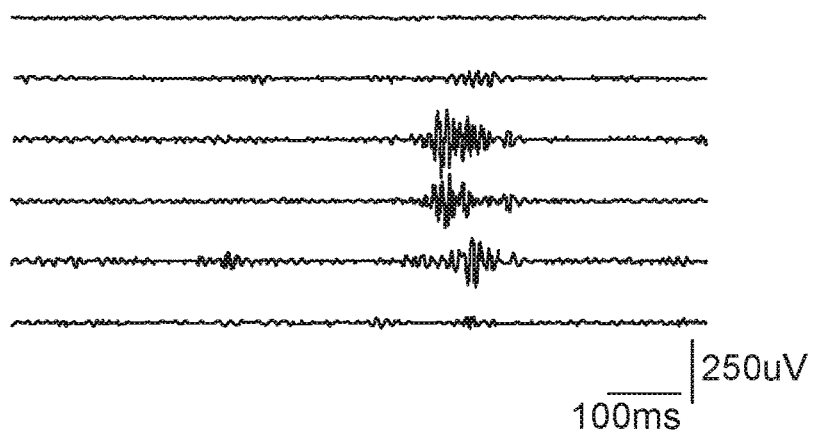

FIGS. 3A-3C depict visual identification of the interictal HFOs. At the conventional setting of 1.6-70 Hz and 10 seconds per page, as depicted in FIG. 3A, segment 300 shows a clear spike. Segment 300 is expanded to reveal more detail in FIGS. 3B and 3C. Changing the time base to 2 seconds per page with the same filter settings shows rhythmic oscillations suggestive of HFOs in FIG. 3B. At the high frequency setting of 50-300 Hz and 2 seconds per page, the presence of discrete HFOs is confirmed in FIG. 3C.

The HFO channels were then classified as HFO+ (channels that showed subsequent evolution of activity) or HFO− (channels that did not show evolution). In other words, a channel was classified as HFO+ when clear-cut HFO activity (>70 Hz) was seen at seizure onset, followed by continuation of the HFO activity or its evolution into the CFA (≤70 Hz) in the same channel until the appearance of the first behavioral change.

Figure 4:
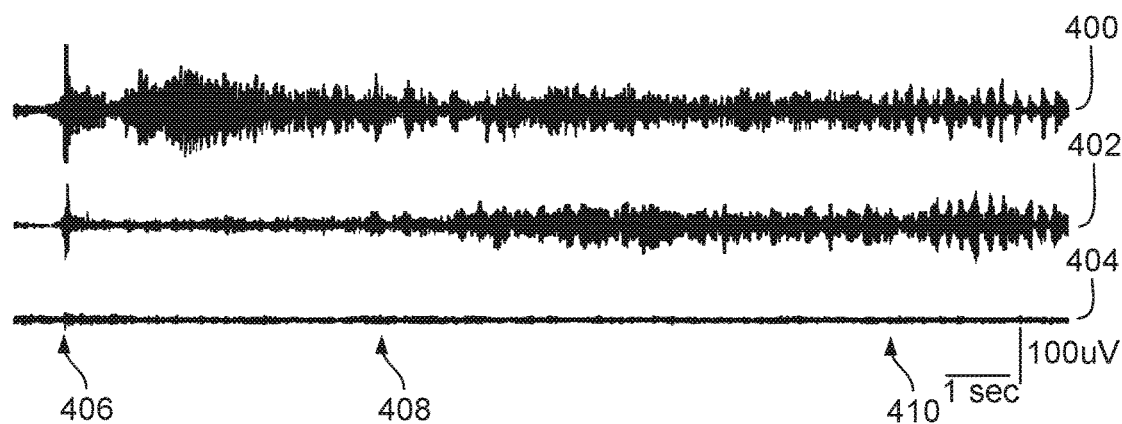
FIG. 4 depicts determination of the seizure onset zone (SOZ) based on the ictal high-frequency oscillations (HFOs).
Figure 5A:
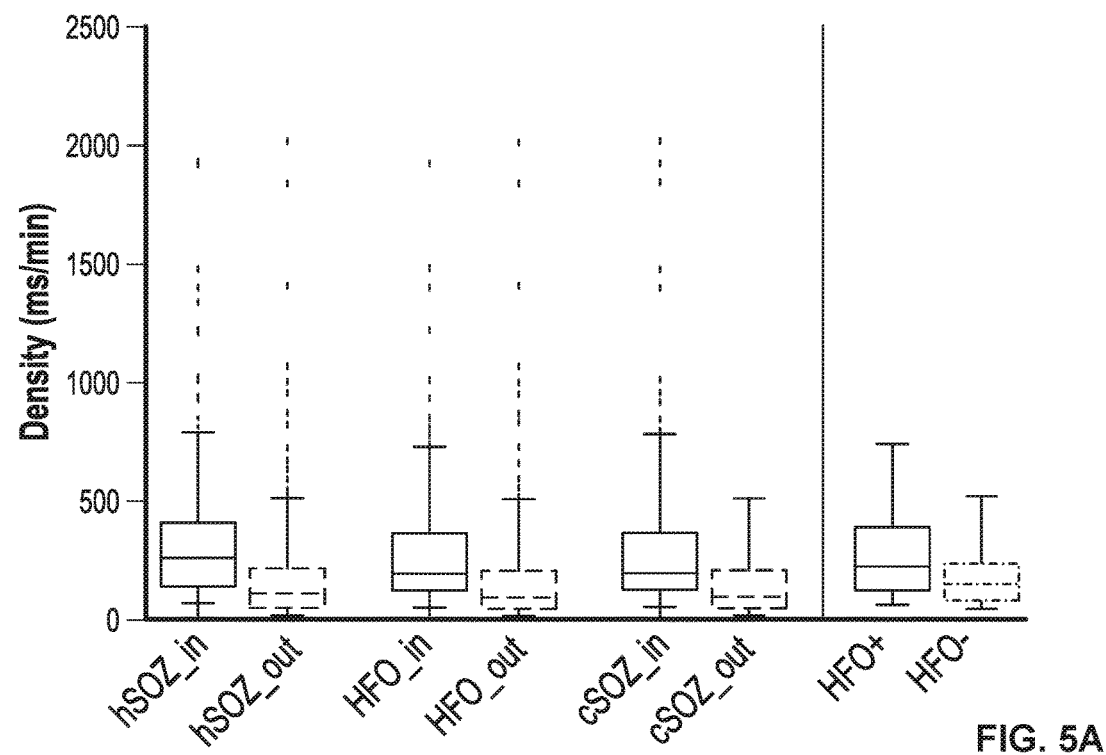
FIGS. 5A-5E depict characteristics of the interictal HFOs in the determination of the SOZ.
Figure 5B:
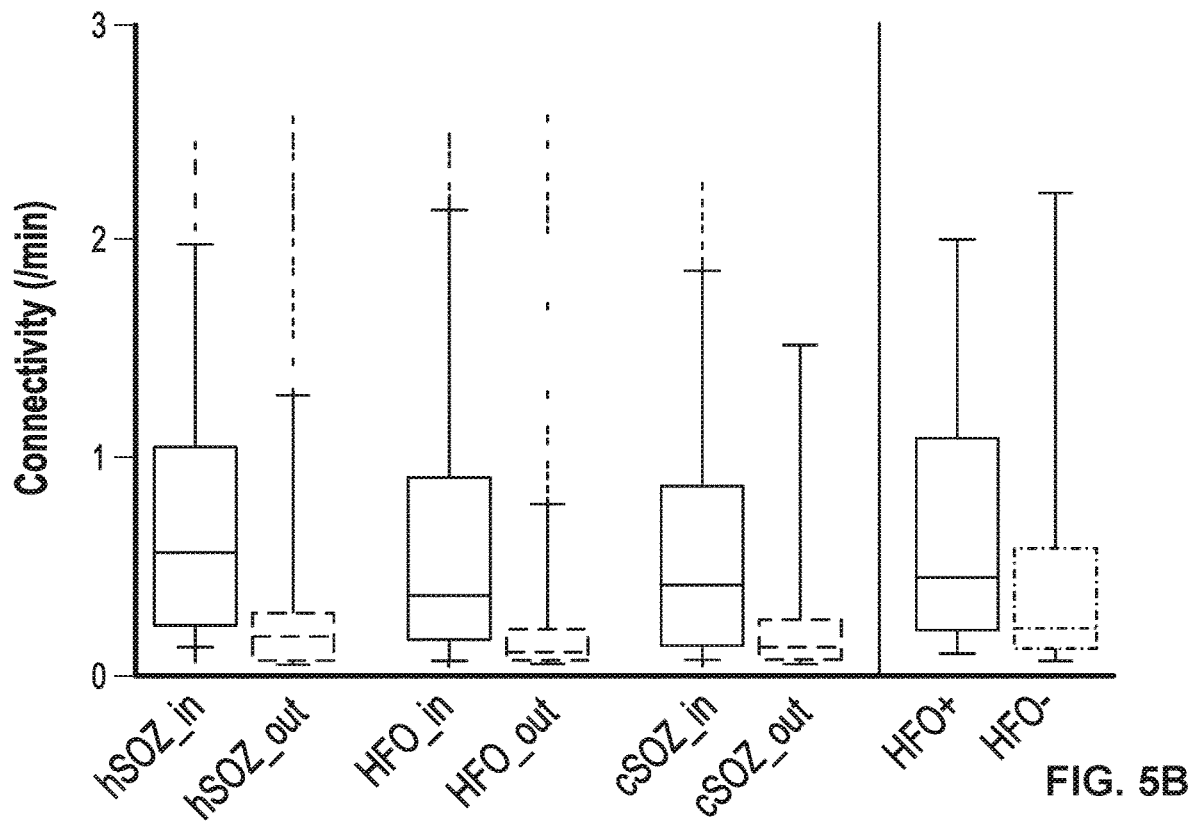
Figure 5C:
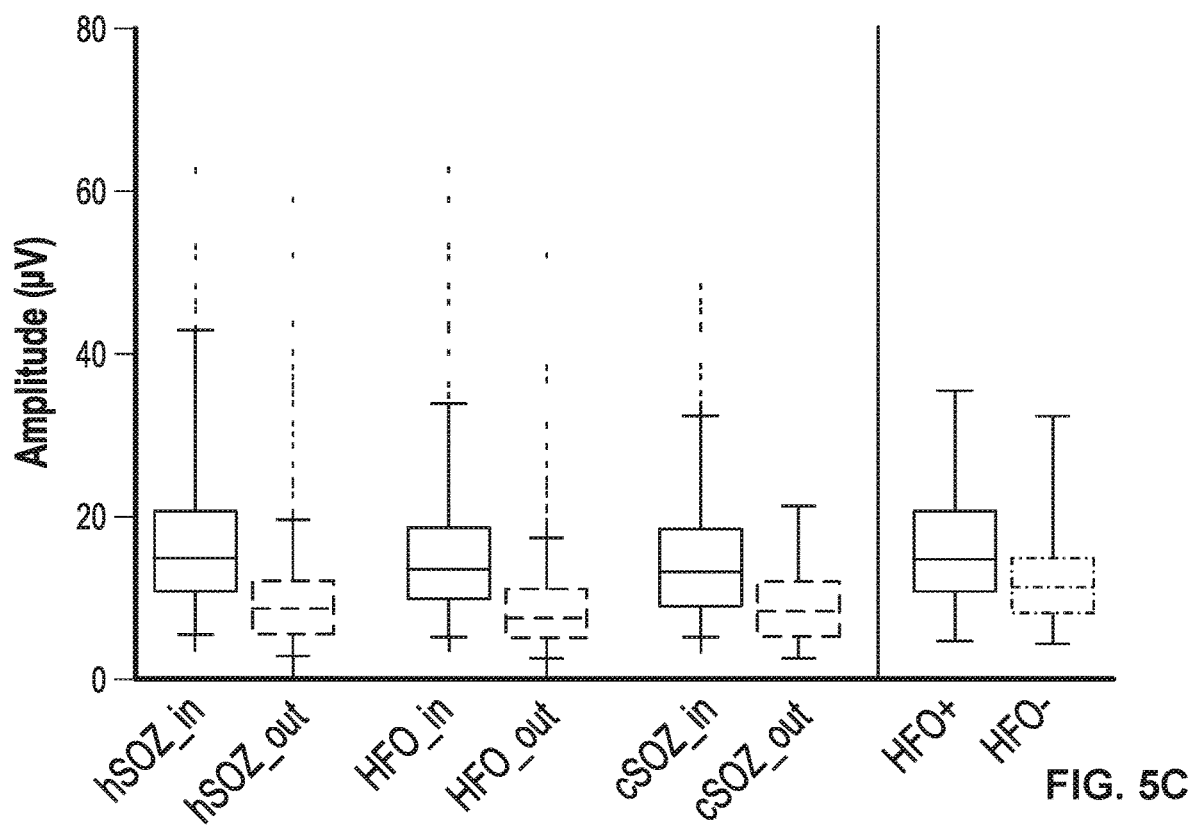
Figure 5D:
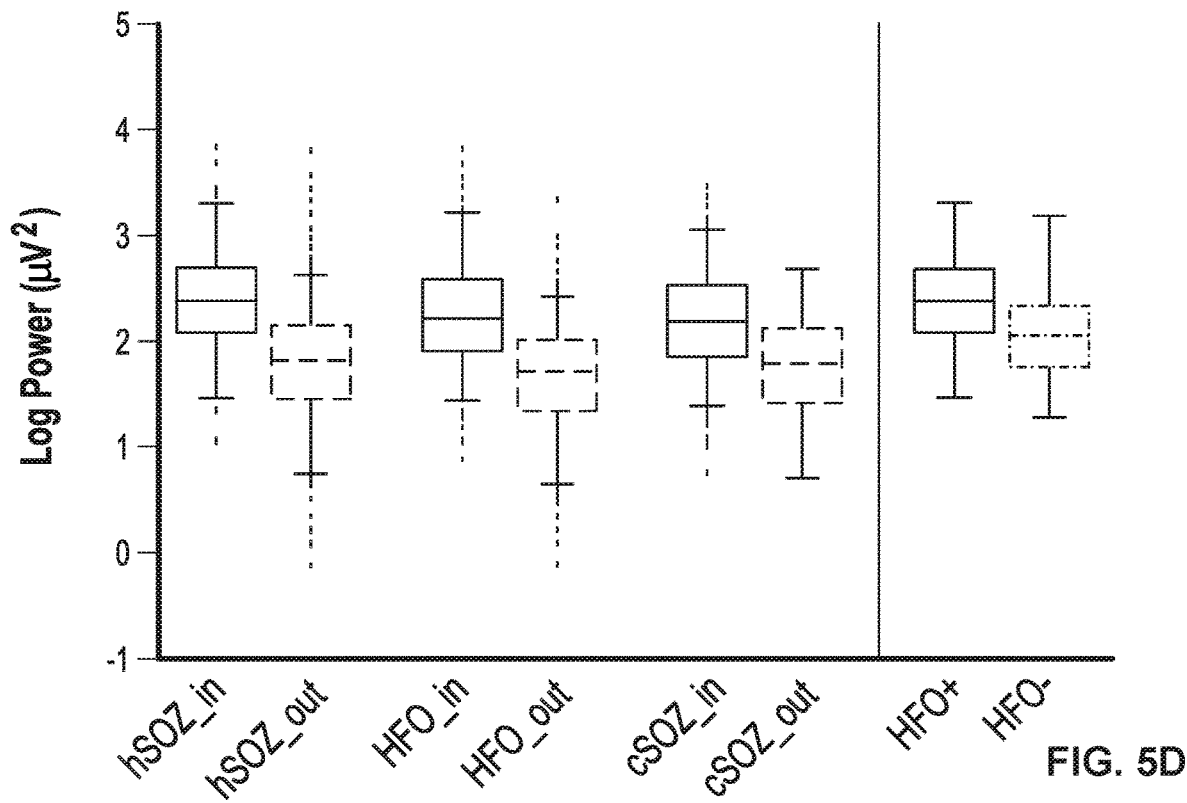
Figure 5E:
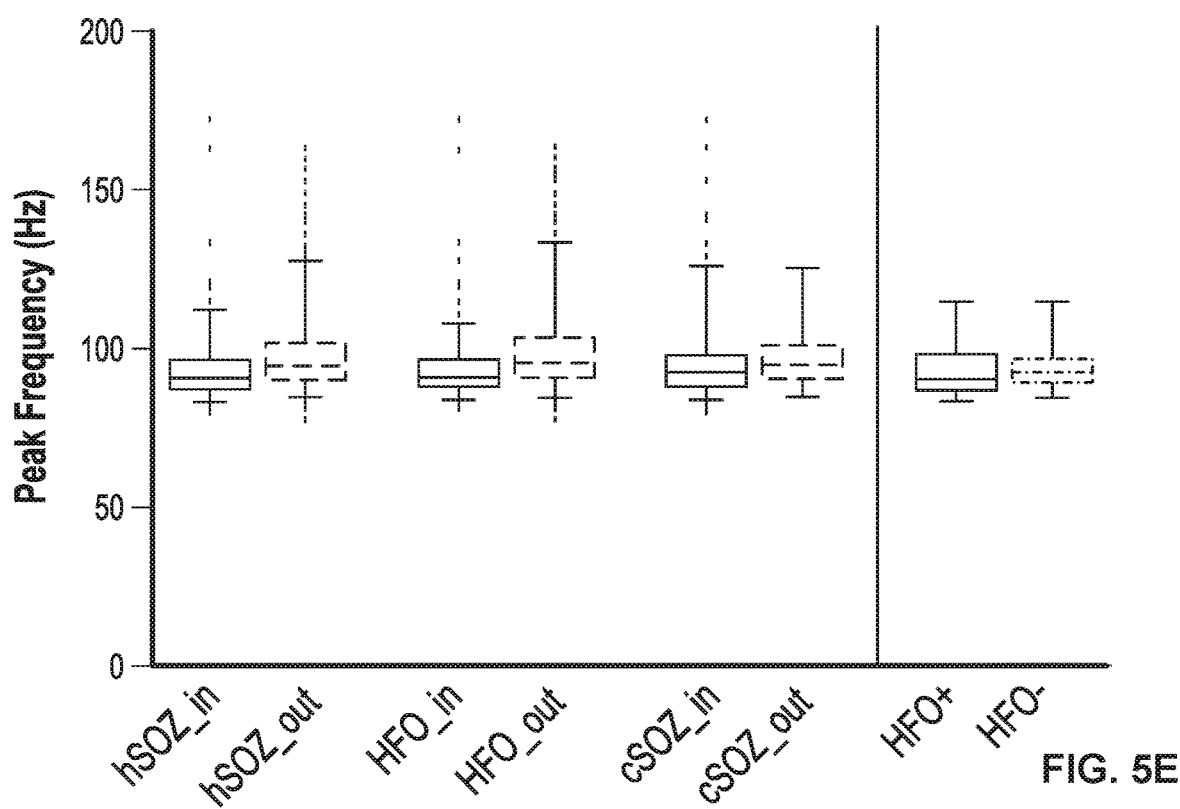
Figure 6A:
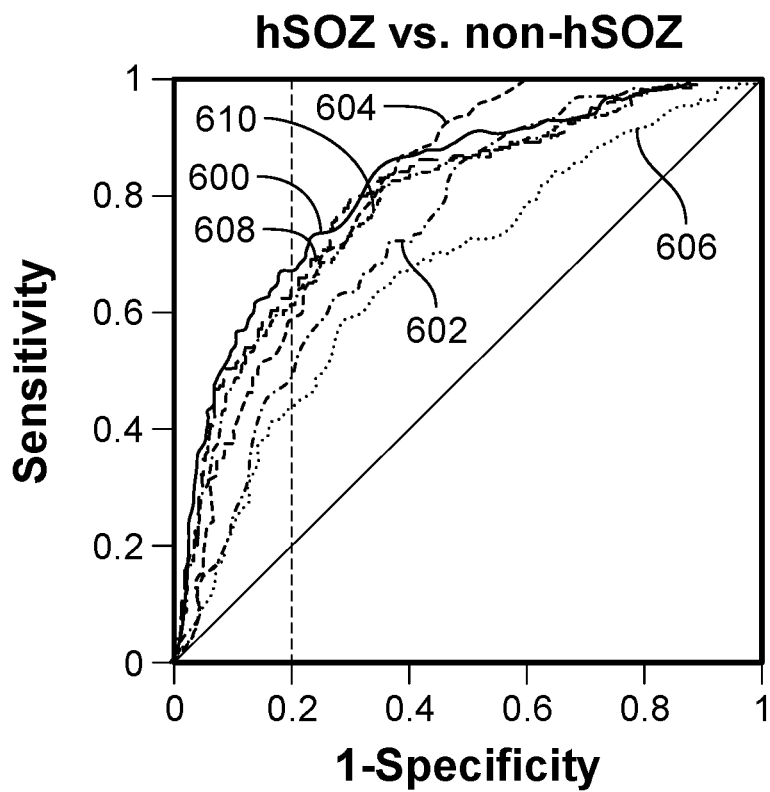
FIGS. 6A-6D shows receiver operating characteristic (ROC) curves for the spatial classification of channels.
Figure 6B:
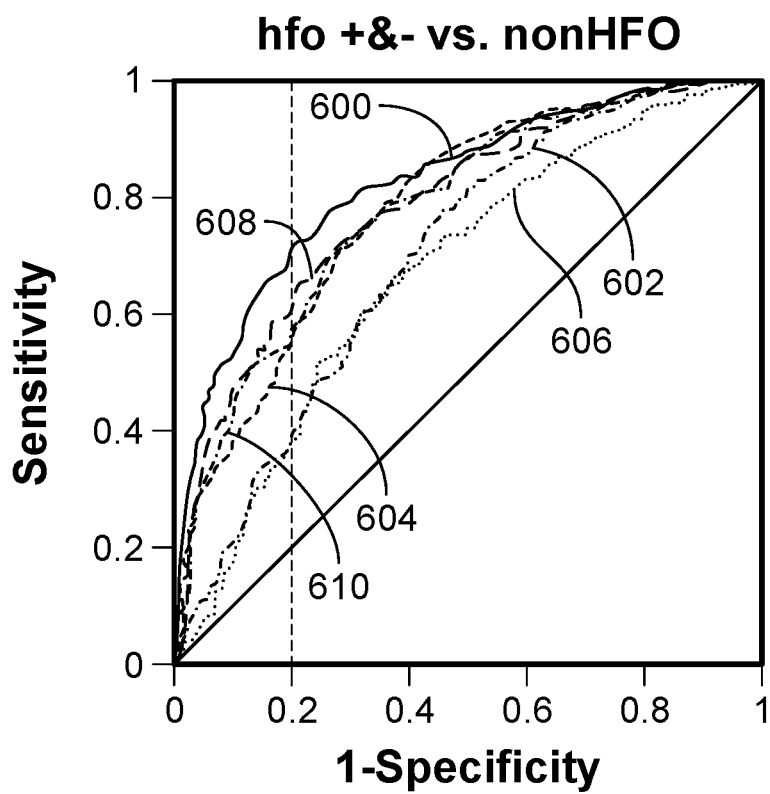
Figure 6C:
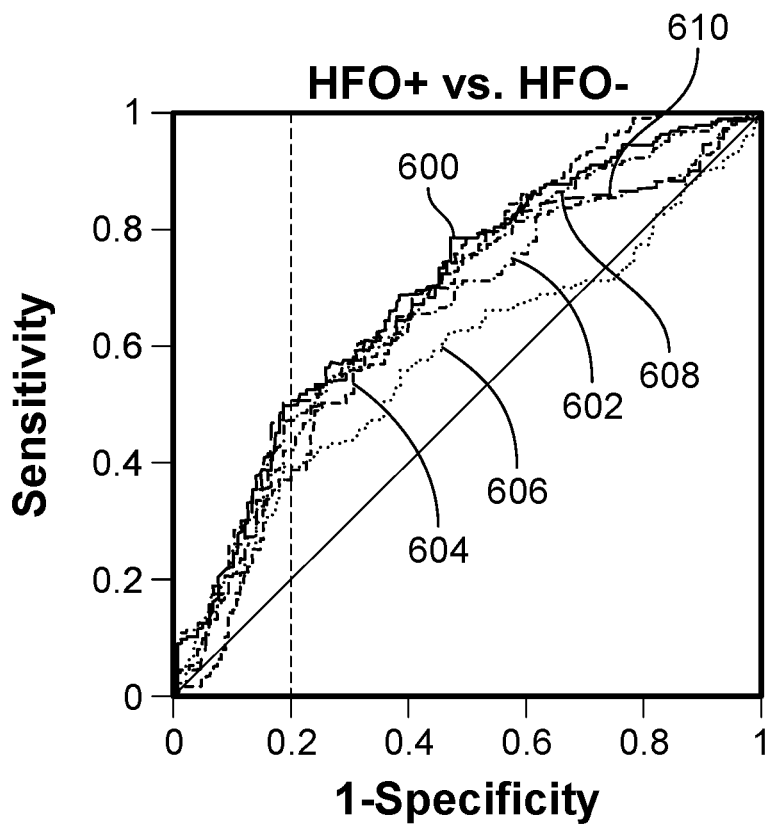
Figure 6D:
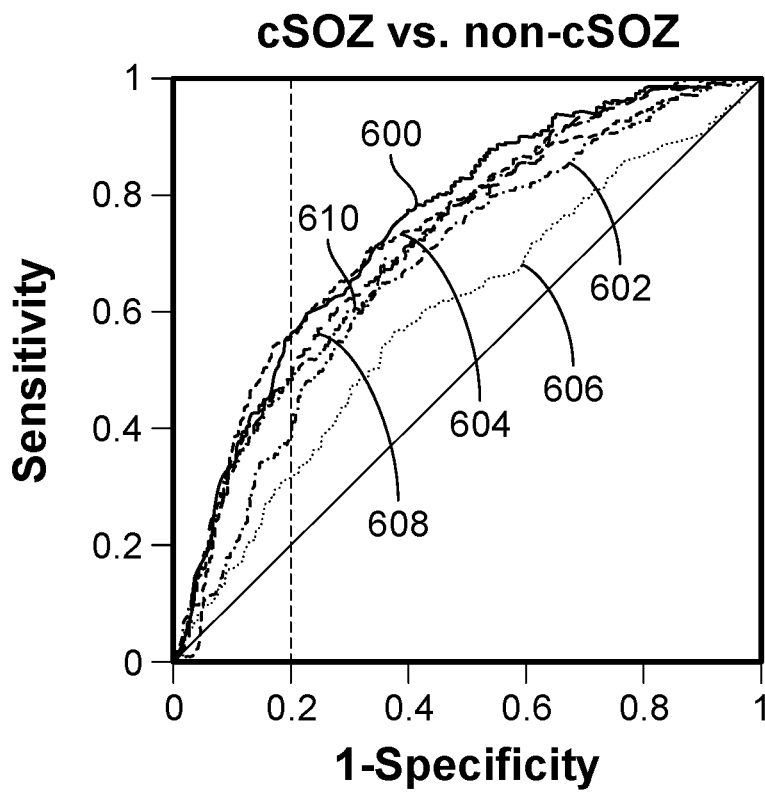

FIG. 4 depicts determination of the SOZ based on the HFOs. At the high frequency setting of 50-300 Hz, rhythmic HFOs are seen at seizure onset in the top and middle channels 400 and 402, respectively (ictal HFO channels), but not in the bottom channel 404 ("HFO seizure onset" 406). Initially, the ictal HFOs evolve in the top channel (i.e., HFO+) but not in the middle channel (i.e., HFO−) which becomes involved a few seconds later at 408. At the time of appearance of clinical symptoms ("clinical seizure onset" 410), the top and middle channels remain involved in the seizure, with evolution of ictal HFOs into the slower, conventional frequency activity (CFA). In this example, the top channel would be classified as HFO+ and CFA, the middle channel as HFO− and CFA, and the bottom channel as non-ictal.

Multiple seizures were analyzed for each subject, and if a given channel was classified as HFO+ for one seizure but HFO− for another seizure, its final designation was HFO+. HFO+ channels from all the seizures were combined to determine the definitive SOZ. Thus, by visual inspection, each channel was classified during the seizure as: HFO+, HFO−, CFA, or non-ictal. The ictal vs. non-ictal and HFO+ vs. HFO− classifications were mutually exclusive; however, an HFO+ or HFO− channel could also be classified as CFA. Based on the channel classification, the SOZs were defined as follows: hSOZ (comprised of HFO+ channels only), hfo+&−SOZ (comprised of both HFO+ and HFO− channels), and cSOZ (comprised of CFA channels).

Automated Detection of Interictal HFOs.

Raw unfiltered EEG recordings were uploaded into MATLAB 2011b (MathWorks, Natick, Mass.) after converting the native vendor file formats to the EDF+ format. After visual inspection using the bipolar montages, those channels that were heavily contaminated by artifact were excluded from further analysis. The EEG was bandpass-filtered at 50-333 Hz using the Butterworth 6-order zero-phase digital filter. Notch filter was applied to remove the 60-Hz line noise and its harmonics. The Hilbert transform was then calculated for each channel. A threshold function, 2 standard deviations above the mean Hilbert signal, was applied to identify the segments that would qualify as HFOs. Only the segments that were ≥9-ms long and contained at least six peaks (two of which being ≥4 standard deviations above the mean rectified EEG signal) were considered as candidate HFOs, and retained for further analysis. Segments that were <14-ms apart were combined into a single detection. A candidate HFO segment was classified as a definite HFO if its mean frequency was >70 Hz or its total power in the 70-333-Hz frequency range was greater than the total power in the <70-Hz frequency range (calculated by the fast Fourier transform [FFT]). For segments >512-ms long, the FFT was performed on partial segments of data using 512-ms width and 50% window overlap. If any sub-segment satisfied the criteria for an HFO, then the entire segment was classified as an HFO. All segments detected as definite HFOs along with those that were considered as HFOs but ultimately rejected were separately identified and displayed. Several different combinations of energy functions (Hilbert transform, root mean square, and line length) and threshold parameters (standard deviation and Tukey inner and outer fence) were tried, but the most consistent and reliable HFO detections were obtained using the Hilbert transform with the settings described above. Detection of so-called "false HFOs" caused by the filtering of sharp artifacts was reduced by visually removing the sections of data with signal discontinuities and persistent sharp artifacts, and by mandating that the detected HFOs contain at least six rectified peaks above the mean signal threshold.

Validation of the Detection Algorithm.

Two experienced epileptologists validated the performance of the algorithm. Rater 1 participated in the algorithm development, whereas rater 2 did not. Each rater evaluated a one-minute data segment in two randomly selected, high-firing and low-firing channels in five subjects. A custom graphical user interface allowed the raters to scroll through the data, one channel at a time, in one-second epochs. The raters were asked to indicate if the computer-marked segments represented the HFOs (including both the definitive and putative HFOs), and were also given the opportunity to freely designate any additional segments that should have been designated as HFOs that the computer missed. Using this method, the algorithm had 77-91% sensitivity, 96-98% specificity, and 93-97% accuracy between the two raters. The concordance between the computer and the raters was "substantial" (kappa: 0.68; rater 2) or "perfect" (kappa: 0.84; rater 1).

Selection of HFO Features.

Density, connectivity, peak frequency, log power, and amplitude, defined herein, were identified to characterize the interictal HFOs.

Extraction of HFO Features.

The HFO features were extracted from the archived data from a training cohort of 10 subjects with temporal and extratemporal epilepsy. For each subject, a 20-minute interictal file was analyzed, each file consisting of discontinuous data segments of variable length (each 30-60 seconds), sampled intermittently (every 15-30 minutes) for several hours over multiple days. The number and dose of the antiepileptic drugs varied when the interictal recordings were obtained. The archived data did not allow for the awake and sleep state distinction. Using the automated method, the HFOs in each channel were detected, and the features were extracted. Each feature was compared inside vs. outside the various SOZs (i.e., hSOZ, hfo+&−SOZ, and cSOZ) and between the HFO types (HFO+ vs. HFO−) using the Mann-Whitney U-test in GraphPad Prism (GraphPad Software, La Jolla, Calif.). p values <0.05 were considered to be significant.

Logistic Regression Models for Spatial and Temporal Classification.

Binomial logistic regression (BLR) models were created based on the HFO features derived from the training cohort in SPSS (IBM Corporation, Armonk, N.Y.). For the spatial classification of channels, all the five features were entered into the model with SOZ as the dependent variable, and performed the following comparisons: hSOZ vs. non-hSOZ channels; hfo+&−SOZ vs. non-hfo+&−SOZ channels; cSOZ vs. non-cSOZ channels; and HFO+ vs. HFO− channels. To measure the strength of association between the predicted probabilities and the classification, the receiver operating characteristic (ROC) curves were plotted for each feature and for all the features considered together. The classification of the SOZ channels was constrained to have high specificity by selecting the cutoff point on the ROC curve that corresponded to the sensitivity at the 0.8 specificity on the x-axis.

Evaluation of Prediction Performance.

The prediction performance of the BLR models was tested in a separate replication cohort of three subjects. For reproducibility, two interictal files were collected for each subject from different days, each file 20 minutes long, consisting of a single continuous data segment (unlike the training interictal file which was discontinuous). To test the model performance in the replication cohort, the regression coefficients derived from the training cohort were used to obtain the probabilities of prediction. From a practical standpoint, the goal was to test the applicability of the group-level models to predict in a novel test subject whether or not a given channel will be classified as a SOZ channel before the first seizure occurred. Once the first seizure occurs in the test subject, the SOZ channels will be known, limiting the further utility of the group-level models unless a second, independent SOZ exists. The prediction performance was assessed using the F1 measure, which is the harmonic mean of recall (i.e., sensitivity) and precision (i.e., positive predictive value), given by:

$$F1 = \frac{2 \cdot R \cdot P}{R + P}$$

where R (recall) is given by TP/(TP+FN) and P (precision) is given by TP/(TP+FP), where TP represents true positives, FN represents false negatives, and FP represents false positives. The value of the F1 measure ranges from 0 to 1, with 1 suggestive of best performance.

Results.

Among 24 consecutive subjects who underwent intracranial monitoring, 10 subjects met the inclusion criteria for the training cohort. Fourteen subjects were excluded because of: inadequate data sampling rate (n=5), lack of seizures during monitoring (n=2), or insufficient archived interictal data (n=7). For the replication cohort, three recent consecutive subjects were identified. Subjects 1-5 were included in a previous study. The median number of channels analyzed was 83 (range: 59-100) in the training cohort and 76 (range: 55-94) in the replication cohort. Among 822 available channels in the training cohort, 15 were excluded due to persistent artifacts, leaving 807 channels for analysis: 211 HFO+, 159 HFO−, 307 CFA, and 130 non-ictal channels. Among 228 available channels in the replication cohort, three were excluded due to persistent artifacts, leaving 225 channels for analysis: 49 HFO+, 34 HFO−, 72 CFA, and 70 non-ictal channels.

Table 1 lists characteristics of subjects in the training and replication cohorts. Training cohort included Subjects 1-10. Replication cohort included Subjects 1R-3R.

TABLE 1

| | | | | | | | | | Channel classification | | |
|---|---|---|---|---|---|---|---|---|---|---|---|
| | | Epilepsy | | | Electrodes | Channels | Intracranial | Intracranial | | | |
| Pt | Age/ Sex | duration (years) | MRI | Engel outcome | implanted (n) | analysed, (n) | recording sites | seizure onset zone | HFO+ (n) | HFO− (n) | CFA (n) |
| 1 | 32/M | 30 | Normal | III | 88 | 66¶ | Left F-P convexity, PF, MF, LT Right*: MF, LF | Left frontal | 29 | 24 | 40 |
| 2 | 26/F | 22 | Normal | II | 128 | 84 | Right: F-P convexity, OF, MF, LT, MT, ST, insula Left*: MF, LF | Right inferior and lateral temporal | 4 | 27 | 11 |
| 3 | 19/F | 6 | Right parietal FCD and nodular heterotopia | I | 96 | 82 | Right: P-O convexity, LT, ST, MO | Right parieto-occipital | 27 | 34 | 54 |
| 4 | 20/M | 17 | Normal | II | 124 | 99 | Left: F-P convexity, PF, MF, LT Right*: MF, LF | Left frontal | 35 | 30 | 52 |
| 5 | 19/M | 12 | Normal | I | 128 | 87¶ | Right: F-P convexity, LT, ST, LP, LO, MO | Right posterior temporal-occipital | 46 | 6 | 51 |
| 6 | 38/M | 36 | Right MTS; subtle left MTS | I | 96 | 77 | Right: F-P convexity, LT, MT, ST Left*: MT | Right: inferomesial and lateral temporal | 12 | 4 | 9 |
| 7§ | 19/F | 17 | Left MTS | I | 84 | 73 | Left: F-T convexity, LT, MT, ST | Left inferomesial temporal | 12 | 11 | 18 |
| 8 | 91/M | 8 | Normal | I | 116 | 95 | Left: F-P convexity, PF, LT, MT Right*: MT | Left mesial and lateral temporal | 6 | 13 | 15 |
| 9 | 18/M | 15 | Bilateral hippocampal signal hyperintensity | I | 72 | 59 | Right: LF, LT, MT Left*: LT, MT | Right mesial and lateral temporal | 11 | 10 | 23 |

TABLE 1-continued

Characteristics of subjects in the training and replication cohorts.

| Pt | Age/ Sex | Epilepsy duration (years) | MRI | Engel outcome | Electrodes implanted (n) | Channels analysed, (n) | Intracranial recording sites | Intracranial seizure onset zone | Channel classification | | |
|---|---|---|---|---|---|---|---|---|---|---|---|
| | | | | | | | | | HFO+ (n) | HFO− (n) | CFA (n) |
| 10 | 41/M | 40 | Right P-O EM; right MTS; | I | 124 | 100 | Right: F-P convexity, LO, LT, MT Left*: MT | Right posterior temporal-parietal; Independent right anterolateral temporal | 29 | 0 | 34 |
| 1R | 23/M | 19 | Subtle left MTS | III | 108 | 94 | Left: F-P convexity, OF, LT, MT, ST Right*: LT | Left lateral temporal | 8 | 2 | 23 |
| 2R | 37/M | 22 | Left perisylvian heterotopia | I | 86 | 76¶ | Left: F-P convexity, PF, LT, ST, Intralesional | Left parietal | 31 | 25 | 38 |
| 3R | 54/F | 37 | Normal | I | 68 | 55¶ | Right: LT, ST, LO, LP | Right lateral temporal | 10 | 7 | 11 |

§Reoperation after failed prior left selective amygdalohippocampectomy.
*Limited coverage.
¶Implantation included only subdural electrodes (note that all other subjects had both subdural and intracerebral depth electrodes).
FCD: focal cortical dysplasia;
EM: encephalomalacia;
MTS: mesial temporal sclerosis;
HFO: high-frequency oscillation;
CFA: conventional frequency activity;
F-P: fronto-parietal;
P-O: parieto-occipital;
PF: prefrontal;
MF: medial frontal;
LF: lateral frontal;
OF: orbitofrontal;
LP: lateral parietal;
LT: lateral temporal;
MT: mesial temporal;
ST: subtemporal;
LO: lateral occipital;
MO: medial occipital;
LP: lateral parietal.

Characteristics of Interictal HFOs.

The interictal HFO features inside the SOZ differed significantly from those outside the SOZ. The values of density, connectivity, amplitude, and log power were higher inside the SOZs (hSOZ, hfo+&−SOZ, and cSOZ) than outside, whereas the peak frequency was lower inside the SOZs than outside ($p<0.0001$). Density and connectivity showed 2-4-fold differences in the absolute values, being higher inside than outside the SOZs. The HFOs in the HFO+ channels showed higher density, connectivity, amplitude, and log power ($p<0.0001$) but lower peak frequency ($p<0.05$) than those in the HFO channels.

FIGS. 5A-5E depict characteristics of the interictal HFOs. Results of Mann-Whitney U test are shown for the five features (density, connectivity, peak frequency, log power, and amplitude) for the spatial classification of channels as inside vs. outside the various SOZs. The bottom and top edges of each box correspond to the 25th and 75th percentile values respectively; the bottom and top whiskers correspond to the 5th and 95th percentile values respectively; the horizontal line within the box represents the median; dots on either side of the whiskers represent the outliers. All the differences were significant ($p<0.05$). In FIGS. 5A-5E, the following abbreviations are used: hSOZ in: inside hSOZ; hSOZ out: outside hSOZ; HFO in: inside hfo+&−SOZ; HFO out: outside hfo+&−SOZ; cSOZ in: inside cSOZ; cSOZ out: outside cSOZ; HFO+: ictal HFOs with evolution; HFO−: ictal HFOs without evolution.

Spatial Classification of the SOZs.

In the training cohort, the model containing all the five interictal HFO features reliably differentiated the channels located inside the SOZ from those outside the SOZ ($p<0.001$). The respective accuracy and ROC area under curve (AUC) of the group models were: 81% and 0.81 for the classification of hSOZ; 76% and 0.82 for the classification of hfo+&−SOZ; 70% and 0.75 for the classification of cSOZ; and 62% and 0.69 for the classification of HFO+ vs. HFO− channels.

FIGS. 6A-6D show the ROC curves for the spatial classification of channels, with plots 600, 602, 604, 606, 608 and 610 indicating all variables, density, connectivity, frequency, log power, and amplitude, respectively. The ROC curves correspond to the group-level logistic regression models in the training cohort. The curves are obtained from the interictal HFO features individually and together for the spatial classification of channels localized to inside vs. outside the different seizure onset zones (hSOZ, hfo+&− SOZ, and cSOZ), and for the differentiation of HFO+ vs. HFO− channels. The dashed, vertical line corresponds to the 0.8 specificity cutoff.

Individually, the log power and connectivity were the most useful differentiating features. Log power had the odds ratio (OR) of 20.5, 14.5, and 11.8 for the classification of hSOZ, hfo+&−SOZ, and cSOZ, respectively. Connectivity had the OR of 1.7, 5.9, and 1.6 for the classification of hSOZ, hfo+&−SOZ, and cSOZ, respectively.

Prediction of the SOZs.

Figure 7:
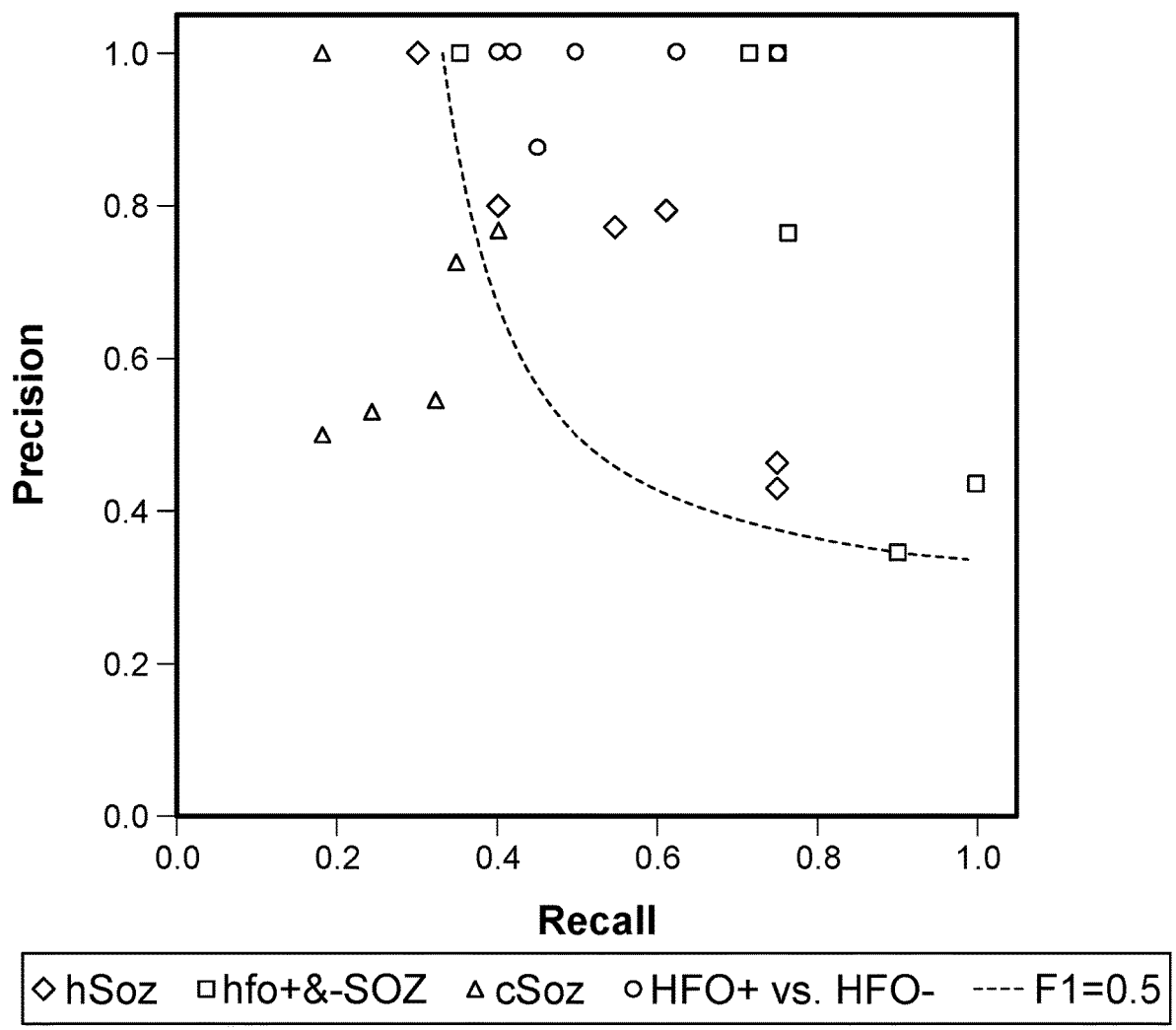
FIG. 7 is a plot showing performance of a classification model for the determination of the SOZ.
Figure 8A:
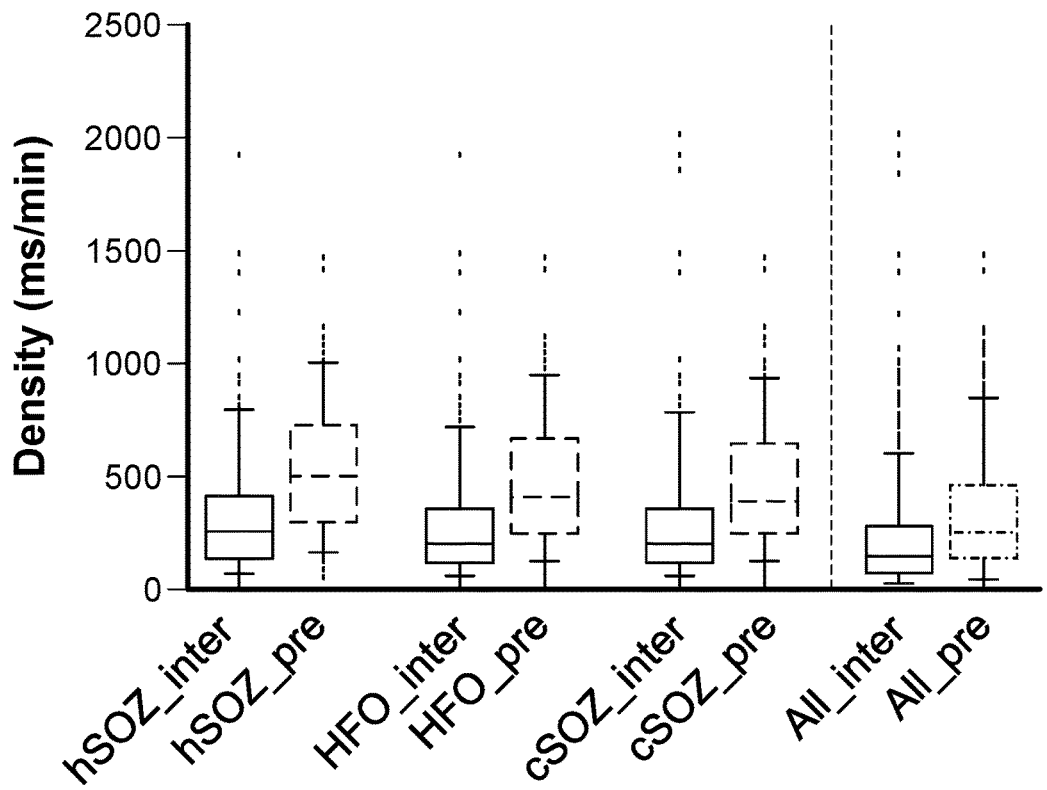
FIGS. 8A-8E show Mann-Whitney U test results for density, connectivity, peak frequency, log power, and amplitude for the differentiation of the preictal and the interictal states.
Figure 8B:
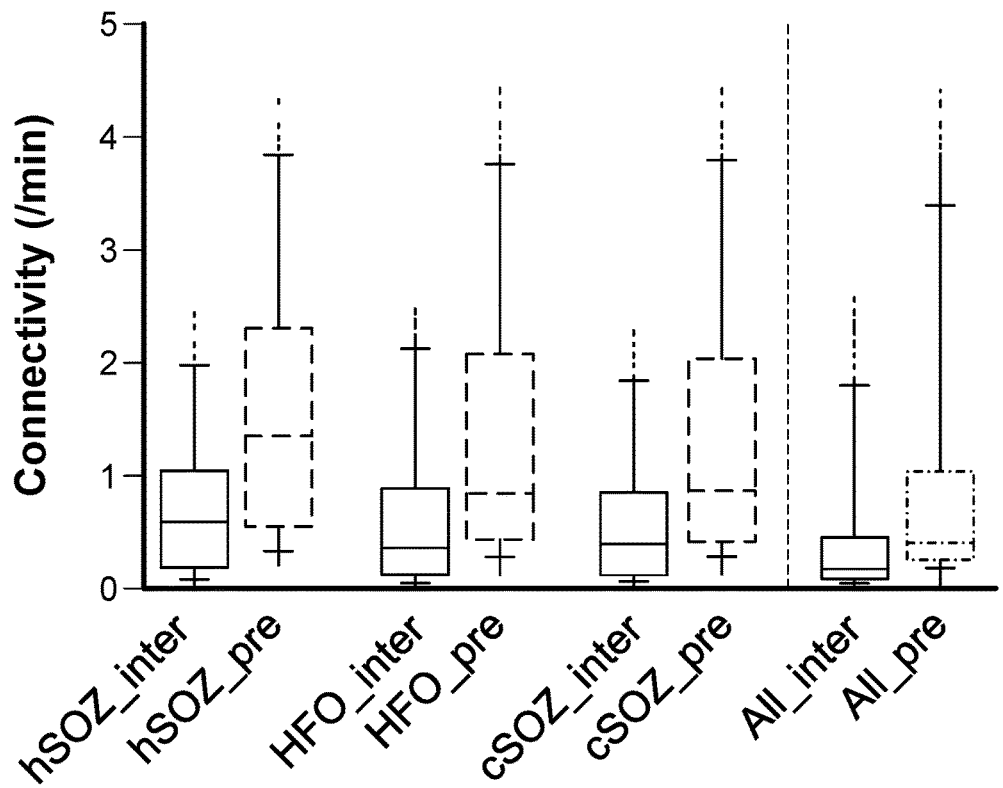
Figure 8C:
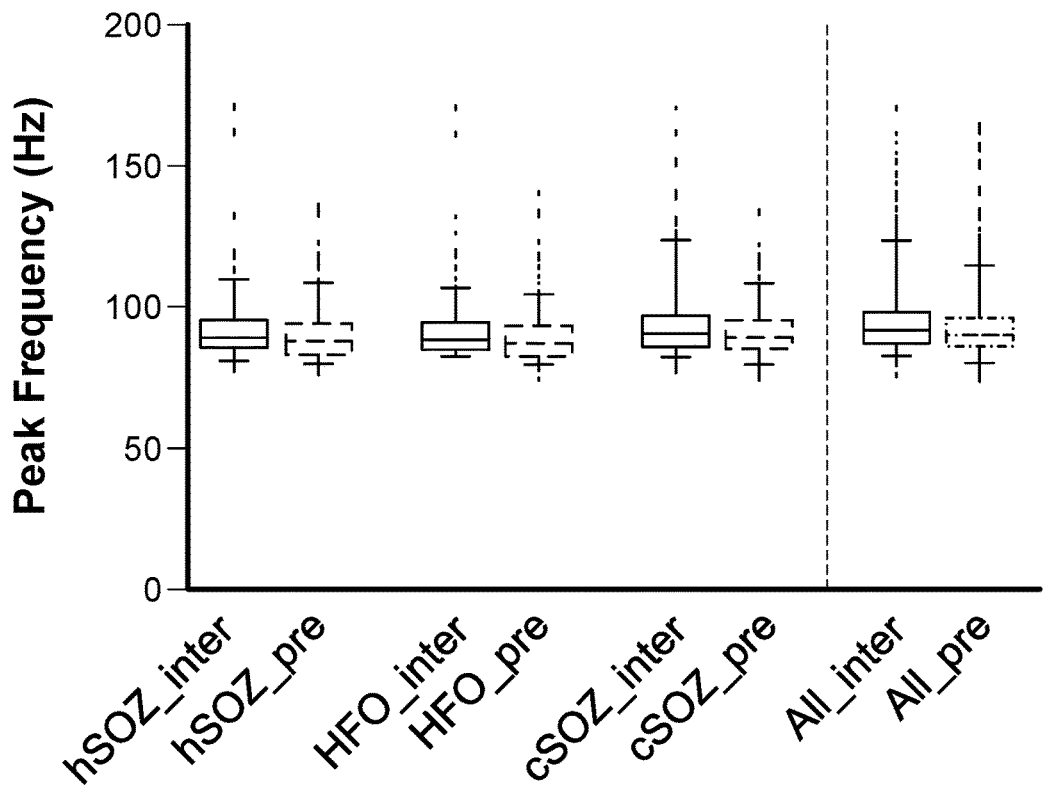
Figure 8D:
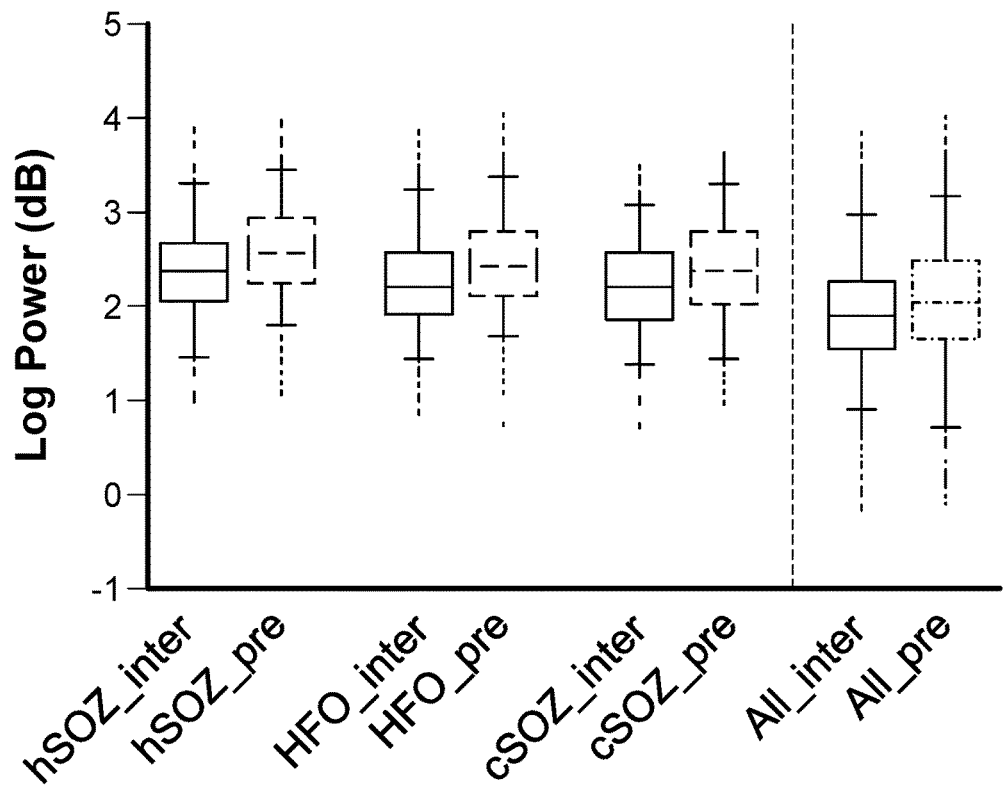
Figure 8E:
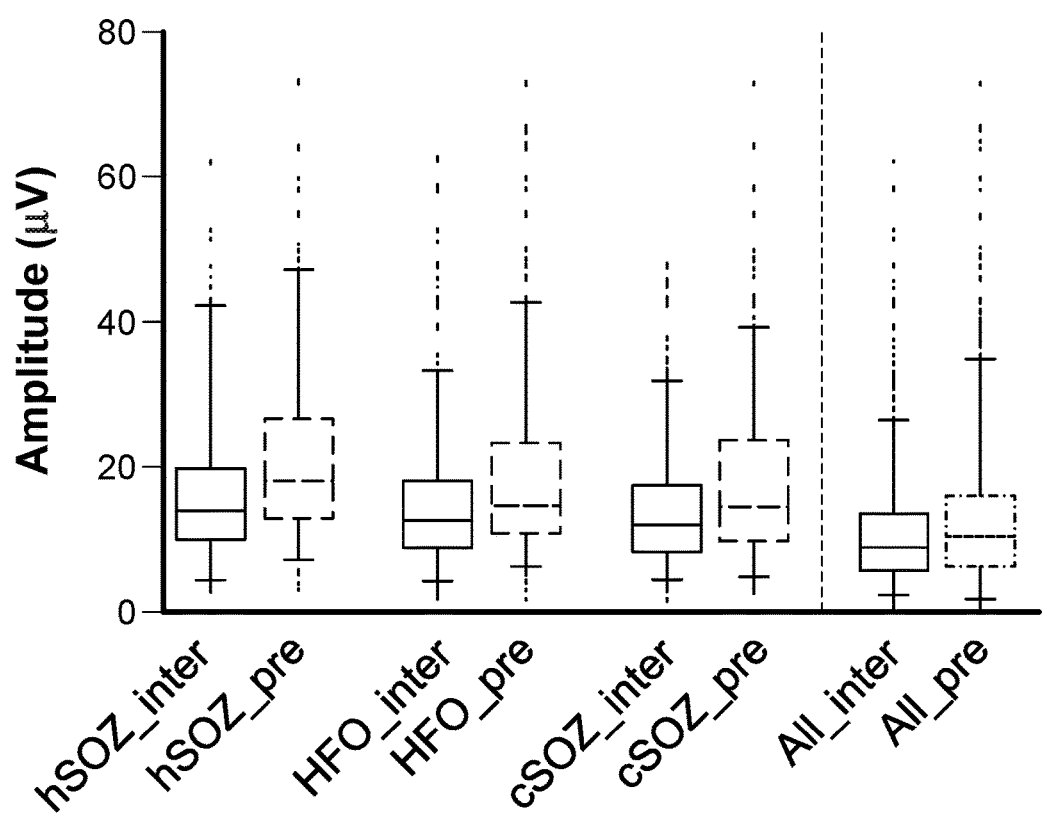

The performance of the classification models of the training cohort was tested by applying them to the replication cohort consisting of novel subjects. The coefficients derived from the group-level BLR models of the training cohort were used to calculate the probability of a given channel being in one of the SOZs (hSOZ, hfo+&−SOZ, and cSOZ) or of a particular type (HFO+ vs. HFO−). The datasets from the three subjects in the replication cohort are shown in FIG. 7. The datasets indicated by the plotted values above and to the right of the dotted line, which corresponds to F1=0.5, were considered to have been classified reliably. In FIG. 7, hSOZ data points are represented by diamonds, hfo+&−SOZ data points are represented by squares, and cSOZ data points are represented by triangles. HFO+ vs. HFO− data points are represented by circles. The F1 measures showed some variability across subjects, but were largely similar in each subject within a given category. Analysis of the two datasets for each subject showed that the classifier was able to differentiate the HFO+ channels from the HFO− channels in all three subjects (F1 0.57-0.86), predict the hfo+&−SOZ channels in three subjects (F1 0.50-0.86), and predict the hSOZ channels in two subjects (F1 0.57-0.69). However, the classifier was not reliable in predicting the cSOZ channels (F1 0.27-0.53).

Interictal HFOs as Spatial Predictors of the SOZ.

The above results indicate that multiple HFO features can differentiate the SOZ channels from the non-SOZ channels, with higher classification accuracy for the HFO-defined SOZs than the cSOZ. The HFO density in a given channel was several folds higher inside the SOZ, but was not a discriminating feature in the logistic regression analysis. The HFO connectivity among the channels was found to be a differentiating feature between the SOZ and non-SOZ channels, suggesting the presence of a tightly linked HFO network inside the SOZ, likely reflecting underlying epileptogenicity. The log power was a discriminatory feature for the SOZ channels, but the amplitude (similar to the power) was not, suggesting that the HFO morphology is useful for localizing the SOZ. At a sampling rate of 1000 Hz, the median frequency range of the HFOs in the study was 90-95 Hz. The peak HFO frequency was found to be lower inside the SOZ. This is consistent with the general understanding that pathological HFOs, which are likely to be prevalent inside the SOZ, typically have lower mean frequencies than physiological HFOs. The findings support the notion that the interictal HFO rate, morphology, and network properties are useful spatial markers of the SOZ, particularly the HFO-defined SOZ.

Application of the group models from the training cohort to the replication cohort yielded reliable prediction of the spatial extent of hfo+&−SOZ in all three subjects. These results suggest an "epileptic HFO network" which seems to be expressed not only ictally but also interictally.

Interictal HFOs as Predictors of the Ictal HFO Type.

The interictal HFO features were able to differentiate the HFO+ channels from the HFO− channels with a moderate degree of accuracy. Application of the group models from the training cohort to the replication cohort also yielded reliable differentiation of the HFO+ and HFO− channels in all three subjects. This strengthens the notion of an "epileptic HFO network" mentioned above, and provides a valuable method for localizing the more clinically meaningful type of the ictal HFO-defined SOZ.

In summary, these results highlight the ability of interictal HFOs to define the spatial extent of the SOZ, and to predict with reasonable certainty whether or not a given channel in a novel subject would be involved in the seizure (particularly with the HFO+ type activity) before the first seizure occurs. This holds promise for subjects who fail to have seizures despite chronic invasive monitoring or those who cannot tolerate it for longer periods. The findings also suggest a tight linkage between the interictal HFOs and the HFO-defined SOZ. As the pathological HFOs are generally understood to be specific to epilepsy, and to be generated by mechanisms that are distinct from those of the conventional EEG activity, an understanding of the epileptic HFO network enhances the knowledge of epileptogenesis and ictogenesis. Presence of such a network suggests placing implantable devices for epilepsy treatment (i.e., closed-loop neuromodulation device and seizure prediction system) in close proximity to the HFO-defined SOZ. Because the interictal HFOs are more tightly linked to the HFO-defined SOZ as shown herein, knowledge of the spatial extent of the interictal HFO network can be beneficial in tailoring the location of these devices.

Prediction of Preictal State Based on HFOs

Using interictal HFOs as temporal markers, the presence of a preictal state, distinct from the interictal state, was demonstrated to precede the seizure onset in a cohort of subjects with temporal and extratemporal epilepsies. An automated method to detect the interictal HFOs from multiple simultaneous EEG channels was developed, which allowed processing of large datasets while minimizing the human bias. Multiple features of the HFO events were extracted by an automated method. Those features include density, connectivity, peak frequency, amplitude, and log power. Each HFO event in each EEG channel was characterized in terms of these features to construct an HFO profile. Using the data from a training cohort of subjects, BLR models were created based on these HFO features to classify the channels as being in the interictal state or the preictal state (i.e., temporal markers of the state). The performance of the interictal HFO-based BLR models was tested in predicting the presence of the preictal state in a separate replication cohort of novel test subjects.

"Interictal state" was defined to be any period in the recording temporally separated from a seizure by at least 2 hours. "Preictal state" was defined to be the 5-minute period immediately preceding the seizure onset. To investigate the HFOs as temporal markers, the HFO profiles in the interictal and preictal states inside the various SOZs were compared separately (hSOZ, hfo+&−SOZ, and cSOZ) and among all implanted channels. The ROC curves were plotted. The classification of the state was constrained to have high sensitivity by selecting the cutoff point on the ROC curve that corresponded to the specificity at the 0.8 sensitivity level on the y-axis of the ROC curve.

The prediction performance of the BLR models was tested in a separate replication cohort of 3 subjects. For reproducibility, two interictal and two preictal files were collected from each subject. The interictal files were obtained on different days, with each file 20 minutes long, consisting of a single continuous data segment (unlike the training interictal file which was discontinuous). Each pre-ictal file was 5 minutes long, consisting of the continuous data segment immediately preceding the seizure onset.

Prior to the first seizure, the applicability of the group-level models from the training cohort was tested as temporal markers to predict whether or not the preictal state exists in the replication cohort. After the first seizure, subject-specific models, tailored to the individual subjects, were used to predict the subsequent preictal states. In general, the HFO features differed significantly between the interictal and preictal states, suggesting that they could serve as potential temporal markers of the state.

FIGS. 8A-8E show the Mann-Whitney U test results for each of the following five features: density, connectivity, peak frequency, log power, and amplitude. The bottom and top edges of each box correspond to the 25th and 75th percentile values respectively; the bottom and top whiskers correspond to the 5th and 95th percentile values respectively; the horizontal line within each box represents the median; dots on either side of the whiskers represent the outliers. Suffixes "_inter" and "pre" refer to the interictal and preictal states respectively inside the various SOZs and among all implanted channels. Table 2 lists group level results for the temporal differentiation between the interictal and preictal states.

TABLE 2

Group level results for temporal differentiation between the interictal and preictal states.

| | hSOZ channels | | HFO+δ-channels | |
|---|---|---|---|---|
| | Interictal | Preictal | Interictal | Preictal |
| Density (ms/min) | 255 (137-409) **** | 499 (293-728) | 191 (117-356) **** | 408 (247-666) |
| Connectivity (/min) | 0.57 (0.23-1.1) **** | 1.4 (0.56-2.3) | 0.37 (0.16-0.91) **** | 0.88 (0.45-2.1) |
| Peak frequency (Hz) | 90 (87-96) 0.19 | 89 (84-96) | 91 (87-96) **** | 89 (85-94) |
| Log power (mV$^2$) | 2.4 (2.1-2.7) **** | 2.6 (2.3-3) | 2.2 (1.9-2.6) **** | 2.5 (2.1-2.8) |
| Amplitude (mV) | 15 (11-21) **** | 19 (14-27) | 13 (9.8-19) **** | 15 (12-24) |

| | cSOZ channels | | All channels | |
|---|---|---|---|---|
| | Interictal | Preictal | Interictal | Preictal |
| Density (ms/min) | 208 (112-364) **** | 388 (240-645) | 142 (65-271) **** | 249 (134-455) |
| Connectivity (/min) | 0.43 (0.14-0.87) **** | 0.89 (0.45-2.1) | 0.17 (0.08-0.48) **** | 0.43 (0.29-1.1) |
| Peak frequency (Hz) | 91 (87-98) 0.09 | 91 (87-97) | 94 (89-99) **** | 91 (87-98) |
| Log power (mV$^2$) | 2.2 (1.9-2.5) **** | 2.4 (2.0-2.8) | 2.0 (1.6-2.3) **** | 2.1 (1.7-2.5) |
| Amplitude (mV) | 13 (9.1-18) **** | 15 (11-25) | 9.9 (5.4-14) **** | 11 (7-17) |

Median (25th-75th percentiles) values are shown.

p values obtained from Mann-Whitney U test are shown in the row below each feature (** = p < 0.0001; * = p < 0.001).

The density, connectivity, amplitude, and log power were higher preictally than interictally inside the various SOZs (hSOZ, hfo+&−SOZ, and cSOZ) and in all of the implanted area (p<0.0001 or <0.001). In contrast, the peak frequency was lower preictally than interictally inside the hfo+&−SOZ and in all of the implanted area (p <0.0001) but not inside the hSOZ or cSOZ (p=ns). Despite the highly significant p values for the 5 features, only density and connectivity showed 1.5-2 fold differences in absolute values, being higher preictally than interictally.

In the training cohort, the BLR model containing all the 5 features of the interictal HFOs reliably differentiated the preictal state from the interictal state (p<0.0001). The accuracy of the group models reached 62%, 74%, 66%, and 65% for the classification based on all implanted, hfo+&−SOZ, hSOZ, and cSOZ channels respectively. Individually, the connectivity was the most significant feature with ORs of 2.7, 1.8, 2.7, and 3.3 for all implanted, hfo+&−SOZ, hSOZ, and cSOZ channels respectively. Table 3 lists logistic regression results for the spatial and temporal classifications of the channels in the training cohort.

TABLE 3

Logistic regression results for the temporal classification of the channels in the training cohort.

| | Temporal classification | | | |
| --- | --- | --- | --- | --- |
| | From all channels | From hfo +&− SOZ channels | From hSOZ channels | From cSOZ channels |
| $c^2$ statistic | 198.8 | 180.4 | 94.9 | 130.3 |
| Regression model accuracy | 62% | 74% | 66% | 65% |
| ROC curve AUC | 0.71 | 0.81 | 0.77 | 0.75 |

AUC: Area under curve
Data show group-level logistic regression and ROC curve analysis using all the features in the training cohort. p = 0.0 for all the comparisons.

Figure 9A:
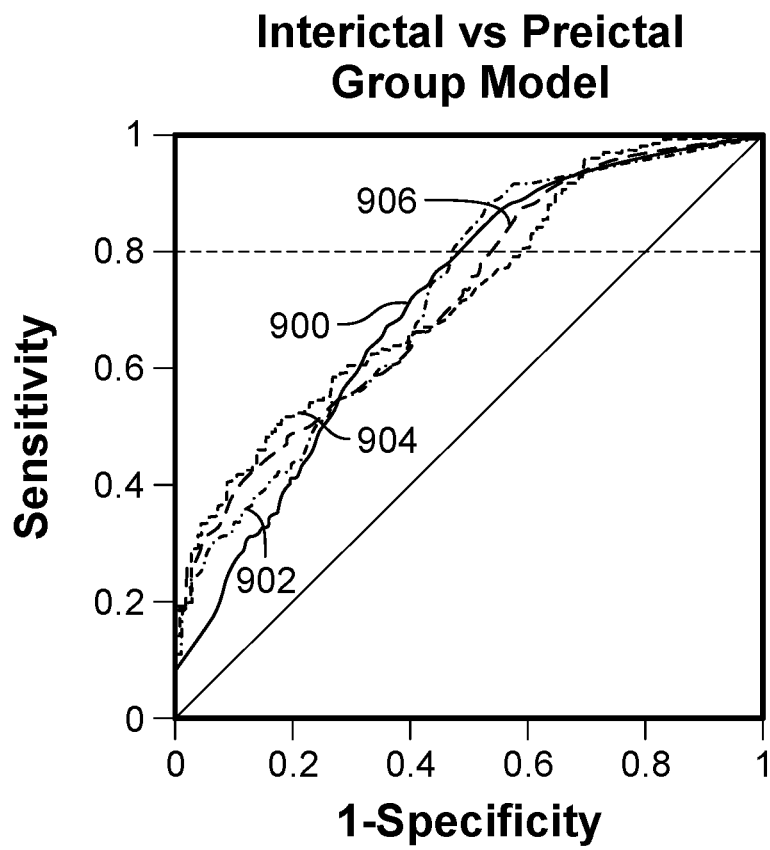
FIGS. 9A-9D show ROC curves for the temporal classification of EEG signals.
Figure 9B:
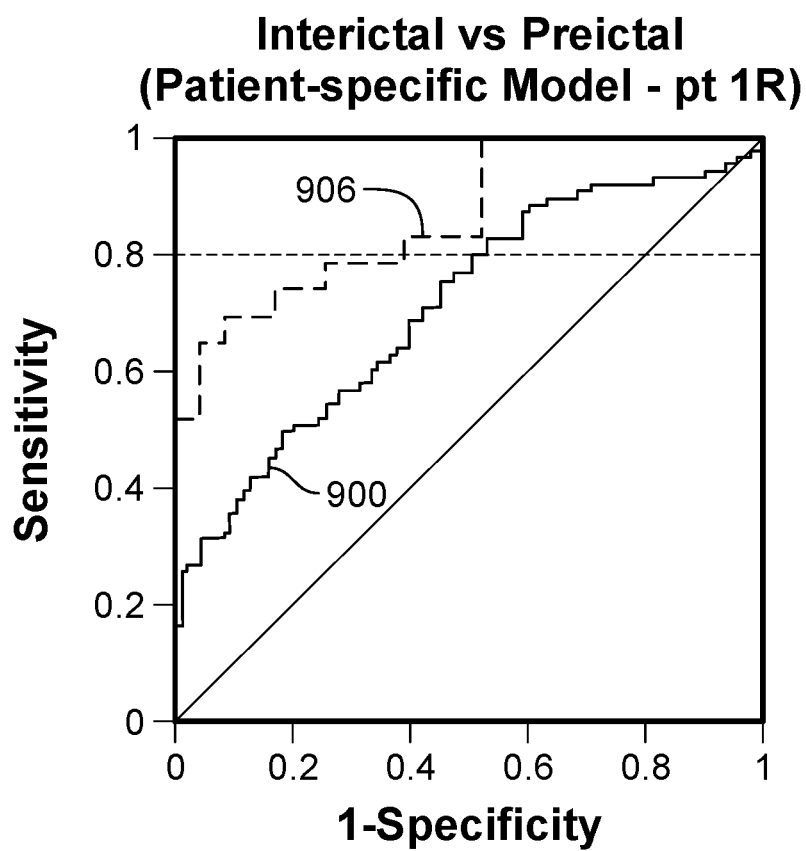
Figure 9C:
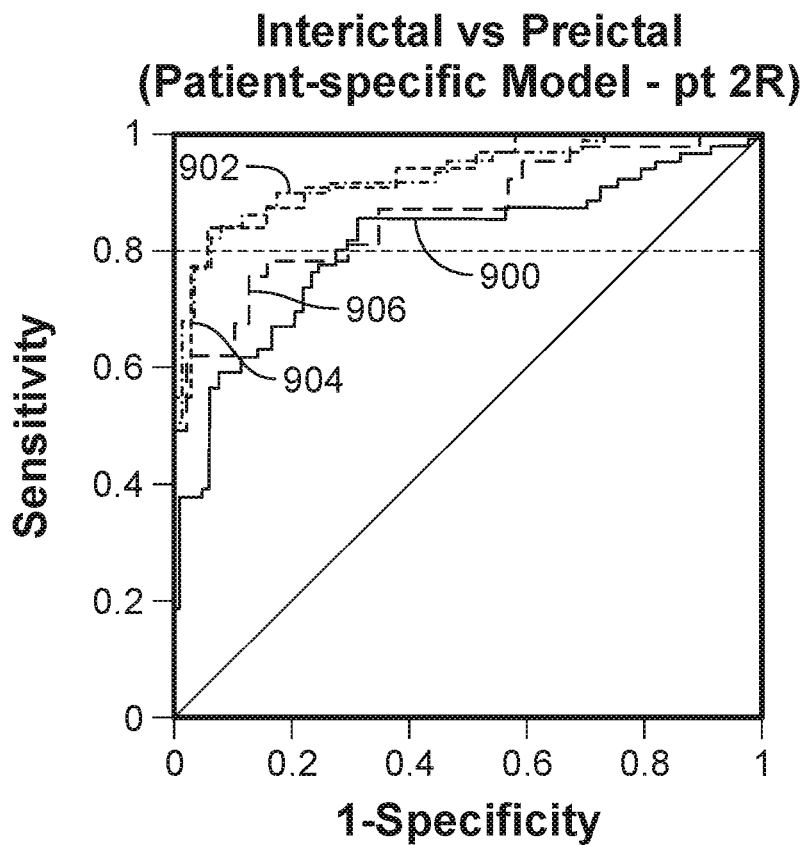
Figure 9D:
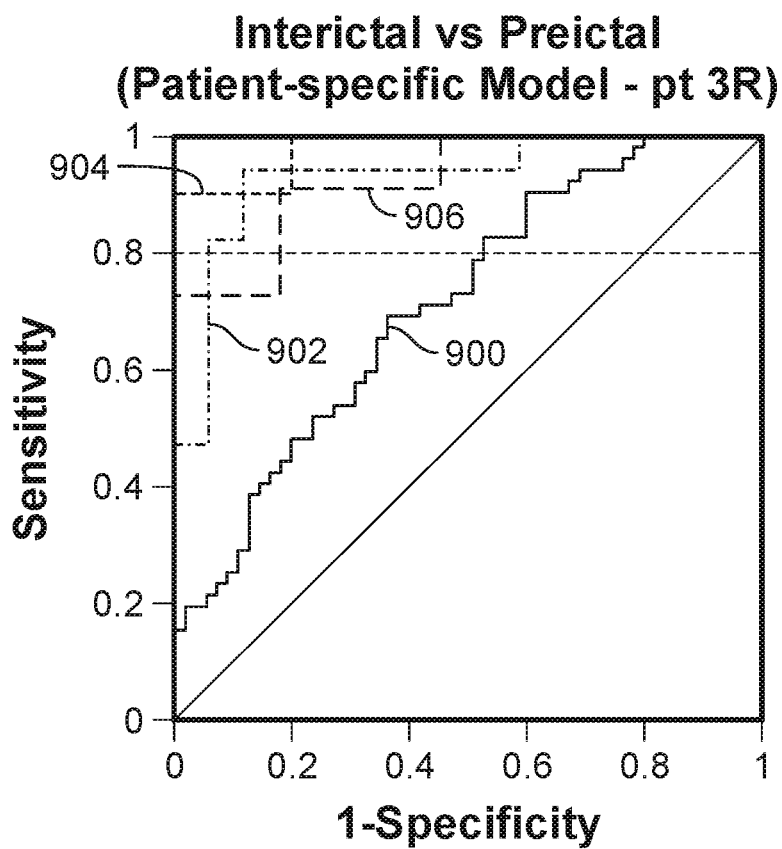
Figure 10A:
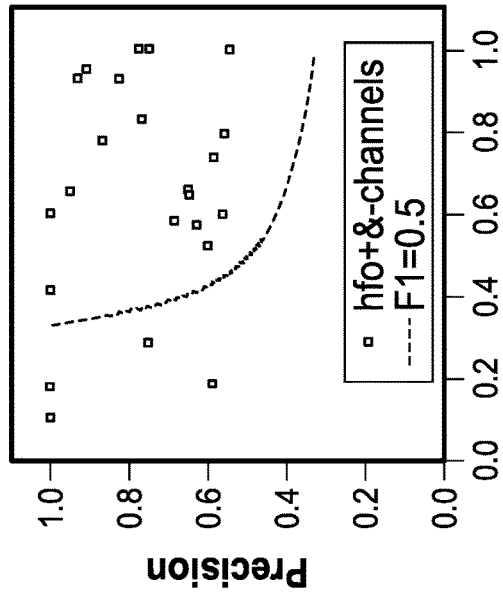
FIGS. 10A-10D shows F1 measures for prediction of the preictal state.
Figure 10B:
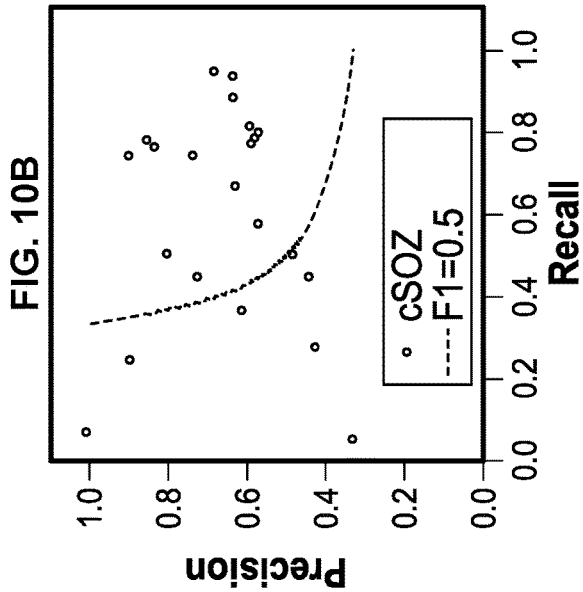
Figure 10C:
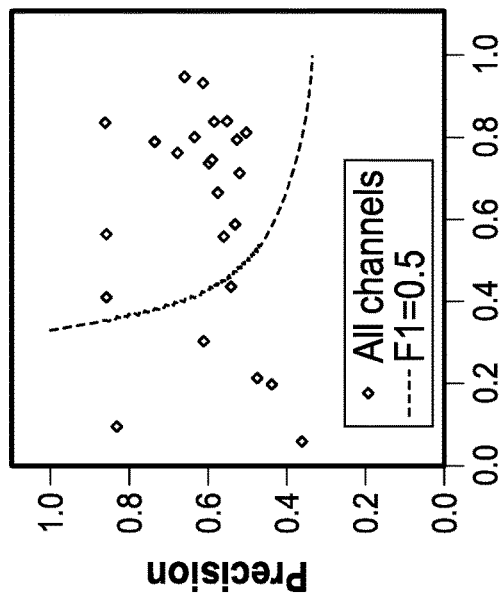
Figure 10D:
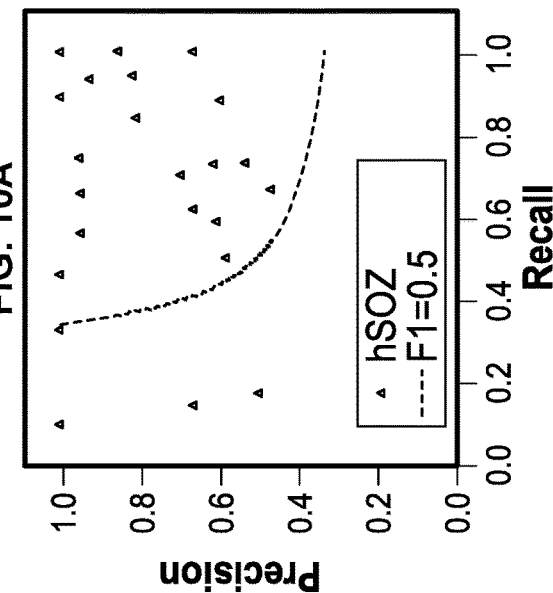

FIGS. 9A-9D show ROC curves for the temporal classification of channels. The ROC curves correspond to the BLR models obtained from the interictal HFO features individually and together for the temporal classification of preictal vs. interictal state based on all implanted, hfo+&−SOZ, hSOZ, and cSOZ channels (plots 900, 902, 904, and 906, respectively). The ROC curves are shown for the group-level model for the training cohort (FIG. 9A) and for the subject-specific models in the replication cohort (FIGS. 9B-9D). The dashed, horizontal line corresponds to the 0.8 sensitivity cutoff. In FIG. 9B, the ROC curves for hfo+&−SOZ and hSOZ channels are not apparent as they hug the left and top edges.

Analysis of the ROC curves obtained from the group models showed that the area under curve (AUC) values were 0.71, 0.81, 0.77, and 0.75 for classification based on all implanted, hfo+&−SOZ, hSOZ, and cSOZ channels respectively (FIG. 9A). Because of the low group-level model accuracies, subject-specific BLR models were created and used for the prediction of subsequent preictal states. These subject-specific models provided much higher accuracies and AUC for the ROC curves (FIGS. 9B-9D).

The performance of the BLR models was evaluated for prediction of the preictal state by applying the coefficients derived from the subject-specific models. Because the models are truly subject-specific, and the subjects had multiple preictal states (depending on the number of seizures), the subject-specific models were validated not only in the replication cohort but also in the training cohort. Thus, 12 subjects were available for testing the temporal prediction performance: 3 from the replication cohort and 9 from the training cohort. Subject #2 from the training cohort was excluded because that subject had only one seizure, yielding only the training dataset but no testing dataset.

Table 4 shows the F1 measures for the temporal prediction of preictal versus interictal state in the replication and training cohorts. Among the 12 subjects, the subject-specific models showed highly variable F1 measures, ranging from 0.09 to 1.00. However, the F1 measure was >0.50 in 79% of the datasets derived from the hfo+&−SOZ or hSOZ channels in contrast to 70% of the datasets derived from all implanted channels and 61% of the datasets derived from the cSOZ channels. FIGS. 10A-10D show F1 measures for prediction of the preictal state. Datasets from the 3 subjects in the replication cohort and 9 subjects from the training cohort are shown. The datasets indicated by the plotted values above and to the right of the dotted line, which corresponds to F1=0.5, were considered to have been classified reliably. Comparison of the two groups of subjects in whom the F1 measure was higher (n=8) versus lower (n=4) showed no significant differences with respect to the number of channels analyzed, the proportion of channels within each SOZ, or the localization of seizure onset in the temporal or extratemporal locations (p=ns, t-test or Fisher's exact test).

TABLE 4

F1 measures for the temporal prediction of preictal versus interictal state in the replication and training cohorts.

| Patient | Sample | From all implanted channels | From hfo +&− SOZ channels | From hSOZ channels | From cSOZ channels |
| --- | --- | --- | --- | --- | --- |
| 1R | 1 | 0.69 | 0.75 | 1.00 | 0.74 |
| | 2 | 0.66 | 0.87 | 0.80 | 0.67 |
| 2R | 1 | 0.55 | 0.30 | 0.49 | 0.38 |
| | 2 | 0.78 | 0.87 | 0.83 | 0.60 |
| 3R | 1 | 0.17 | 0.65 | 0.70 | 0.33 |
| | 2 | 0.28 | x | x | x |
| 1 | 1 | 0.56 | 0.65 | 0.60 | 0.49 |
| | 2 | 0.10 | 0.29 | 0.23 | 0.09 |
| 3 | 1 | 0.72 | 0.80 | 0.94 | 0.80 |
| | 2 | 0.76 | 0.82 | 0.83 | 0.82 |
| 4 | 1 | 0.85 | 0.93 | 0.88 | 0.81 |
| | 2 | 0.68 | 0.58 | 0.70 | 0.62 |
| 5 | 1 | 0.48 | 0.63 | 0.64 | 0.57 |
| | 2 | 0.60 | 0.66 | 0.71 | 0.68 |
| 6 | 1 | 0.74 | 0.86 | 0.63 | 0.44 |
| | 2 | 0.41 | 0.58 | 0.62 | x |
| 7 | 1 | 0.56 | 0.56 | 0.54 | 0.55 |
| | 2 | 0.62 | 0.65 | 0.55 | 0.65 |
| 8 | 1 | 0.67 | 0.70 | 0.92 | 0.76 |
| | 2 | 0.29 | 0.19 | 0.25 | 0.13 |
| 9 | 1 | 0.64 | 0.60 | 0.67 | 0.67 |
| | 2 | 0.62 | 0.41 | 0.17 | 0.46 |
| 10 | 1 | 0.71 | 0.93 | 0.93 | 0.74 |
| | 2 | 0.66 | 0.78 | 0.78 | 0.67 | x = Undetermined since the number of true positives is zero. Subjects 1R-3R belong to replication cohort; subjects 1-10 belong to training cohort.

In a given subject, the interictal HFO profiles, derived from the channels in the ictal HFO-defined SOZ, predicted with reasonable certainty whether or not the preictal state existed, thus suggesting that the interictal HFOs can serve as temporal markers of the preictal state. In particular, multiple HFO features derived from the SOZ channels (density, connectivity, amplitude, and log power) can differentiate the preictal state from the interictal state. Among the HFO features, density (an indicator of the firing rate) and connectivity (a network property) play a significant role in differentiating the preictal from the interictal state.

The temporal variation of the HFOs suggests that it may be possible to predict the state based on the observed features. This hypothesis was tested by investigating whether or not the interictal HFO features can predict the presence of a preictal state. Although group model accuracies were found to be low, higher accuracies were achieved with the use of subject-specific models created from the data obtained after recording the 1$^{st}$ seizure. The performance of the subject-specific models in predicting the preictal state was found to be more reliable when the HFO profiles were derived from the hfo+&−SOZ or hSOZ channels rather than all implanted channels or the cSOZ channels. These results indicate that, in a given subject, the interictal HFO profiles derived from the channels in the HFO-defined SOZ can predict with reasonable certainty whether or not the preictal state exists, supporting the idea that interictal HFOs can serve as temporal markers of the state. Moreover, based on these results, the interictal HFOs are understood to be useful in predicting imminent seizures. The ability of the HFOs to differentiate the state can be expected to have clinical application in the functioning of implantable devices for epilepsy treatment such as a closed-loop neuromodulation device, a seizure prediction system, a seizure-preempting drug delivery system, or a combination thereof.

Further modifications and alternative embodiments of the various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

What is claimed is:

1. A seizure preemption system comprising:
   electrodes for recording simultaneous electroencephalographic (EEG) signals from a subject;
   a controller, electrically coupled to the electrodes and configured to:
     sample the simultaneous EEG signals;
     identify high frequency oscillation (HFO) events in each of the EEG signals;
     extract one or more features from each of the EEG signals to yield HFO profiles for the HFOs recorded from each of the EEG signals, wherein the one or more features comprise a connectivity of each of the EEG signals and at least one additional feature of a group of additional features comprising the group of: density, peak frequency, log power, and amplitude, and connectivity is a measure of the number of the HFO events of the EEG signals that overlap with the HFO events of the other EEG signals; and
     based on the HFO profiles for the EEG signals, identify each of the EEG signals as associated with a preictal state or an interictal state of the subject, wherein the preictal state is a defined length of time immediately preceding the onset of a seizure; and
   a neuromodulator electrically coupled to the controller and configured to deliver electrical stimulations to one or more seizure foci of the subject's brain via one or more of the electrodes in response to identification of at least one EEG signal as associated with a preictal state of the subject wherein:
   the density is a total duration of the HFO events of the EEG signal divided by a duration of the EEG signal;
   the peak frequency is a mean of peak frequencies of the HFO events of the EEG signal;
   the log power is a mean of a logarithm of average power of the HFO events of the EEG signal; and
   the amplitude is a mean of an average amplitude of the HFO events of the EEG signal.

2. The seizure preemption system of claim 1, wherein the interictal state is temporally separated from a seizure by a predefined length of time.

3. The seizure preemption system of claim 1, wherein the electrodes are adapted for intracranial placement.

4. The seizure preemption system of claim 1, wherein the controller is configured to sample the simultaneous EEG signals at a rate sufficient to detect the HFO events.

5. The seizure preemption system of claim 1, wherein the connectivity is given by $$\frac{1}{N} \cdot \frac{1}{t} \sum_{i,j=1, j \neq i}^{N-1} HFO_{ij}$$

where $HFO_{ij}$ represents an overlap between HFO events occurring simultaneously in EEG signals i and j, N is the total number of EEG signals, and t is the total time of all EEG signals analyzed in minutes.

6. The seizure preemption system of claim 5, wherein the overlap occurs when the absolute value of the difference between the starting time of the one of the HFO events in EEG signal i and the starting time of the one of the HFO events in EEG signal j is below a first value or when the absolute value of the difference between the ending time of the one of the HFO events in EEG signal i and the ending time of the one of the HFO events in EEG signal j is below a second value.

7. The seizure preemption system of claim 1, wherein the at least one additional feature comprises the density, wherein the density is the total duration of the HFO events of the EEG signal divided by the duration of the EEG signal.

8. The seizure preemption system of claim 1, wherein the at least one additional feature comprises the peak frequency, wherein the peak frequency is the mean of peak frequencies of the HFO events of the EEG signal.

9. The seizure preemption system of claim 1, wherein the at least one additional feature comprises the log power, wherein the log power is the mean of the logarithm of the average power of the HFO events of the EEG signal.

10. The seizure preemption system of claim 1, wherein the at least one additional feature comprises the amplitude, wherein the amplitude is the mean of the average amplitude of the HFO events of the EEG signal.

11. The seizure preemption system of claim 1, wherein the preictal state and the interictal state are distinct.

12. The seizure preemption system of claim 1, wherein, based on the HFO profiles for the set of EEG signals, the controller is configured to identify each of the EEG signals as associated with a seizure onset zone (SOZ) or a non-SOZ, wherein the SOZ is inside the seizure focus and the non-SOZ is outside the seizure focus.

13. The seizure preemption system of claim 12, wherein identifying each of the EEG signals as associated with a SOZ or a non-SOZ comprises assessing receiver operating characteristic (ROC) curves of the HFO profiles for the set of EEG signals based on a binomial logistic regression (BLR) model of reference HFO profiles with the SOZ as the dependent variable and identifying the SOZ of the subject as corresponding to the location of at least one of the electrodes for which an ROC cutoff exceeds a defined threshold.

14. The seizure preemption system of claim 13, wherein the reference HFO profiles were derived from the subject.

15. The seizure preemption system of claim 1, wherein identifying each EEG signal as associated with a preictal state or an interictal state of the subject comprises assessing a receiver operating characteristic (ROC) of the HFO profiles for the set of EEG signals based on a binomial logistic regression (BLR) model of reference HFO profiles with state as the dependent variable and identifying the preictal state of the subject when an ROC cutoff exceeds a defined threshold.

16. The seizure preemption system of claim 15, wherein the reference HFO profiles were derived from the subject.

17. A seizure prediction system comprising: electrodes for recording simultaneous electroencephalographic (EEG) signals from a subject; and
a controller electrically coupled to the electrodes and configured to: sample the simultaneous EEG signals;
identify high frequency oscillation (HFO) events in each of the EEG signals; extract one or more features from each of the EEG signals to yield HFO profiles for the HFOs recorded from each of the EEG signals, wherein the one or more features comprise a connectivity of each of the EEG signals, and the connectivity is a measure of a number of the HFO events of the EEG signals that overlap with the HFO events of the other EEG signals in the EEG signals;
based on HFO profiles for the EEG signals, identify each of the EEG signals as associated with a preictal state or an interictal state of the subject, wherein the preictal state is defined as a length of time immediately preceding an onset of a seizure: and
based on the HFO profiles for the EEG signals, identify each of the EEG signals as associated with a seizure onset zone (SOZ) or a non-SOZ, wherein the SOZ is inside a seizure focus and the non-SOZ is outside the seizure focus.

18. A system comprising:
electrodes configured to record simultaneous electroencephalographic (EEG) signals from a subject; and
a controller electrically coupled to the electrodes and configured to: sample the simultaneous EEG signals;
identify high frequency oscillation (HFO) events in each of the EEG signals; extract one or more features from each of the EEG signals to yield HFO profiles for HFOs recorded from each of the EEG signals, wherein the one or more features comprise a connectivity of each of the EEG signals, and connectivity is a measure of a number of the HFO events of the EEG signals that overlap with the HFO events of the other EEG signals in the EEG signals; and
based on the HFO profiles for the EEG signals, identify each of the EEG signals as associated with a preictal state or an interictal state of the subject; wherein:
the preictal state is a defined length of time immediately preceding an onset of a seizure; and
identifying each of the EEG signals as associated with the preictal state or the interictal state of the subject comprises assessing a receiver operating characteristic (ROC) of the HFO profiles for the EEG signals based on a binomial logistic regression (BLR) model of reference HFO profiles with the state as a dependent variable and identifying the preictal slate of the subject when an ROC cutoff exceeds a defined threshold.

19. The system of claim 18, further comprising a neuromodulator electrically coupled to the controller and configured to deliver electrical stimulations to one or more seizure foci of the subject's brain via one or more of the electrodes in response to identification of at least one EEG signal as associated with a preictal state of the subject.

20. The system of claim 19, wherein, based on the HFO profiles for the EEG signals, the controller is configured to identify each of the EEG signals as associated with a seizure onset zone (SOZ) or a non-SOZ, wherein the SOZ is inside the seizure focus and the non-SOZ is outside the seizure focus.

* * * * *